United States Patent
Robinson et al.

(10) Patent No.: US 7,027,848 B2
(45) Date of Patent: Apr. 11, 2006

(54) APPARATUS AND METHOD FOR NON-INVASIVE SPECTROSCOPIC MEASUREMENT OF ANALYTES IN TISSUE USING A MATCHED REFERENCE ANALYTE

(75) Inventors: Mark Ries Robinson, Albuquerque, NM (US); Cliona Fleming, Albuquerque, NM (US); Howland Jones, Albuquerque, NM (US); Mark Rohrscheib, Albuquerque, NM (US)

(73) Assignees: InLight Solutions, Inc., Albuquerque, NM (US); University of New Mexico, Albuquerque, NM (US)

( * ) Notice: Subject to any disclaimer, the term of this patent is extended or adjusted under 35 U.S.C. 154(b) by 368 days.

(21) Appl. No.: 10/116,269

(22) Filed: Apr. 4, 2002

(65) Prior Publication Data
US 2003/0191377 A1 Oct. 9, 2003

(51) Int. Cl.
*A61B 5/00* (2006.01)
(52) U.S. Cl. .................................. 600/310; 600/316
(58) Field of Classification Search ................ 600/300, 600/310, 322, 473, 316, 365, 331
See application file for complete search history.

(56) References Cited

U.S. PATENT DOCUMENTS

| | | | |
|---|---|---|---|
| 3,910,701 A | 10/1975 | Henderson et al. | |
| 4,035,083 A | 7/1977 | Woodriff et al. | |
| 4,094,609 A | 6/1978 | Fujii et al. | |
| 4,142,797 A | 3/1979 | Astheimer | |
| 4,169,676 A | 10/1979 | Kaiser | |
| 4,260,220 A | 4/1981 | Whitehead | |
| 4,291,981 A | 9/1981 | Ohnishi et al. | |
| 4,346,998 A | 8/1982 | Franklin | |
| 4,427,889 A | 1/1984 | Muller | |
| 4,537,484 A | 8/1985 | Fowler et al. | |
| 4,598,715 A | 7/1986 | Machler et al. | |
| 4,653,880 A | 3/1987 | Sting et al. | |
| 4,654,530 A | 3/1987 | Dybwad | |
| 4,655,225 A | 4/1987 | Dahne et al. | |
| 4,656,562 A | 4/1987 | Sugino | |

(Continued)

FOREIGN PATENT DOCUMENTS

EP 0 426 358 A2 5/1991

(Continued)

OTHER PUBLICATIONS

Anderson et al., "Reduction of Postprandial Hyperglycemia and Frequency of Hypoglycemia in IDDM Patients on Insulin—Analog Treatment," *Diabetes*, Feb. 1997, vol. 46, No. 2, 14 pages.

(Continued)

*Primary Examiner*—Eric F. Winakur
(74) *Attorney, Agent, or Firm*—Crompton, Seager & Tufte, LLC

(57) ABSTRACT

A method is provided for building improved calibration models or for improving modifications to these models or validation of the models used in the non-invasive spectroscopic measurement of an analyte or attribute of tissue. The method uses a matched reference sample and measurement of that sample to ensure that the correct relationship between the spectra and analyte is made during the model building, modification or calibration process. A matched reference sample is one in which the analyte of interest or attribute of interest in the reference sample is representative of the analyte or attribute at the site being non-invasively sampled or the agreement between the reference concentration and the non-invasively sampled concentration is clinically significant.

32 Claims, 16 Drawing Sheets

U.S. PATENT DOCUMENTS

| | | |
|---|---|---|
| 4,657,397 A | 4/1987 | Oehler et al. |
| 4,661,706 A | 4/1987 | Messerschmidt et al. |
| 4,684,255 A | 8/1987 | Ford |
| 4,712,912 A | 12/1987 | Messerschmidt |
| 4,730,882 A | 3/1988 | Messerschmidt |
| 4,787,013 A | 11/1988 | Sugino et al. |
| 4,787,708 A | 11/1988 | Whitehead |
| 4,830,496 A | 5/1989 | Young |
| 4,853,542 A | 8/1989 | Milosevic et al. |
| 4,857,735 A | 8/1989 | Noller |
| 4,859,064 A | 8/1989 | Messerschmidt et al. |
| 4,866,644 A | 9/1989 | Shenk et al. |
| 4,867,557 A | 9/1989 | Takatani et al. |
| 4,882,492 A | 11/1989 | Schlager |
| 4,883,953 A | 11/1989 | Koashi et al. |
| 4,975,581 A | 12/1990 | Robinson et al. |
| 5,007,423 A | 4/1991 | Branstetter et al. |
| 5,015,100 A | 5/1991 | Doyle |
| 5,019,715 A | 5/1991 | Sting et al. |
| 5,028,787 A | 7/1991 | Rosenthal et al. |
| 5,051,602 A | 9/1991 | Sting et al. |
| 5,068,536 A | 11/1991 | Rosenthal |
| 5,070,874 A * | 12/1991 | Barnes et al. ............... 600/316 |
| 5,109,465 A | 4/1992 | Klopotek |
| 5,158,082 A | 10/1992 | Jones |
| 5,178,142 A | 1/1993 | Harjunmaa et al. |
| 5,179,951 A | 1/1993 | Knudson |
| 5,188,108 A | 2/1993 | Secker |
| 5,204,532 A | 4/1993 | Rosenthal |
| 5,222,496 A | 6/1993 | Clarke et al. |
| 5,223,715 A | 6/1993 | Taylor |
| 5,224,478 A | 7/1993 | Sakai et al. |
| 5,225,678 A | 7/1993 | Messerschmidt |
| 5,237,178 A | 8/1993 | Rosenthal et al. |
| 5,243,546 A | 9/1993 | Maggard |
| 5,257,086 A | 10/1993 | Fateley et al. |
| 5,267,152 A | 11/1993 | Yang et al. |
| 5,268,749 A | 12/1993 | Weber et al. |
| 5,291,560 A | 3/1994 | Daugman |
| 5,303,026 A | 4/1994 | Strobl et al. |
| 5,311,021 A | 5/1994 | Messerschmidt |
| 5,313,941 A | 5/1994 | Braig et al. |
| 5,321,265 A | 6/1994 | Block |
| 5,331,958 A | 7/1994 | Oppenheimer |
| 5,348,003 A | 9/1994 | Caro |
| 5,355,880 A | 10/1994 | Thomas et al. |
| 5,360,004 A | 11/1994 | Purdy et al. |
| 5,361,758 A | 11/1994 | Hall et al. |
| 5,372,135 A | 12/1994 | Mendelson et al. |
| 5,379,764 A | 1/1995 | Barnes et al. |
| 5,402,778 A | 4/1995 | Chance |
| 5,419,321 A | 5/1995 | Evans |
| 5,435,309 A | 7/1995 | Thomas et al. |
| 5,441,053 A | 8/1995 | Lodder et al. |
| 5,452,723 A | 9/1995 | Wu et al. |
| 5,459,317 A | 10/1995 | Small et al. |
| 5,459,677 A | 10/1995 | Kowalski et al. |
| 5,460,177 A | 10/1995 | Purdy et al. |
| 5,483,335 A | 1/1996 | Tobias |
| 5,490,506 A | 2/1996 | Takatani et al. |
| 5,494,032 A | 2/1996 | Robinson et al. |
| 5,507,288 A * | 4/1996 | Bocker et al. ............... 600/322 |
| 5,515,847 A | 5/1996 | Braig et al. |
| 5,523,054 A | 6/1996 | Switalski et al. |
| 5,533,509 A | 7/1996 | Koashi et al. |
| 5,537,208 A | 7/1996 | Bertram et al. |
| 5,552,997 A | 9/1996 | Massart |
| 5,592,402 A | 1/1997 | Beebe et al. |
| 5,596,992 A | 1/1997 | Haaland et al. |
| 5,606,164 A | 2/1997 | Price et al. |
| 5,630,413 A | 5/1997 | Thomas et al. |
| 5,636,633 A | 6/1997 | Messerschmidt et al. |
| 5,655,530 A | 8/1997 | Messerschmidt |
| 5,672,864 A | 9/1997 | Kaplan |
| 5,672,875 A | 9/1997 | Block et al. |
| 5,677,762 A | 10/1997 | Ortyn et al. |
| 5,708,593 A | 1/1998 | Saby et al. |
| 5,719,950 A | 2/1998 | Osten et al. |
| 5,724,268 A | 3/1998 | Sodickson et al. |
| 5,743,262 A | 4/1998 | Lepper, Jr. et al. |
| 5,747,806 A | 5/1998 | Khalil |
| 5,750,994 A | 5/1998 | Schlager |
| 5,772,587 A * | 6/1998 | Gratton et al. ............... 600/310 |
| 5,782,755 A | 7/1998 | Chance et al. |
| 5,792,050 A | 8/1998 | Alam et al. |
| 5,792,053 A | 8/1998 | Skladnev et al. |
| 5,793,881 A | 8/1998 | Stiver et al. |
| 5,808,739 A | 9/1998 | Turner et al. |
| 5,817,007 A | 10/1998 | Fodgaard et al. |
| 5,818,048 A | 10/1998 | Sodickson et al. |
| 5,823,951 A | 10/1998 | Messerschmidt et al. |
| 5,828,066 A | 10/1998 | Messerschmidt |
| 5,830,132 A | 11/1998 | Robinson |
| 5,830,133 A | 11/1998 | Osten et al. |
| 5,850,623 A | 12/1998 | Carman, Jr. et al. |
| 5,853,370 A | 12/1998 | Chance et al. |
| 5,857,462 A | 1/1999 | Thomas et al. |
| 5,860,421 A | 1/1999 | Eppstein et al. |
| 5,886,347 A | 3/1999 | Inoue et al. |
| 5,902,033 A | 5/1999 | Levis et al. |
| 5,914,780 A | 6/1999 | Turner et al. |
| 5,933,792 A | 8/1999 | Andersen et al. |
| 5,935,062 A | 8/1999 | Messerschmidt et al. |
| 5,945,676 A | 8/1999 | Khalil et al. |
| 5,949,543 A | 9/1999 | Bleier et al. |
| 5,957,841 A | 9/1999 | Maruo et al. |
| 5,961,449 A | 10/1999 | Toida et al. |
| 5,963,319 A | 10/1999 | Jarvis et al. |
| 6,005,722 A | 12/1999 | Butterworth et al. |
| 6,016,435 A | 1/2000 | Maruo et al. |
| 6,025,597 A | 2/2000 | Sterling et al. |
| 6,026,314 A | 2/2000 | Amerov et al. |
| 6,031,609 A | 2/2000 | Funk et al. |
| 6,034,370 A | 3/2000 | Messerschmidt |
| 6,040,578 A | 3/2000 | Malin et al. |
| 6,041,247 A | 3/2000 | Weckstrom et al. |
| 6,041,410 A | 3/2000 | Hsu et al. |
| 6,043,492 A | 3/2000 | Lee et al. |
| 6,044,285 A | 3/2000 | Chaiken et al. |
| 6,045,502 A | 4/2000 | Eppstein et al. |
| 6,046,808 A | 4/2000 | Fateley |
| 6,049,727 A | 4/2000 | Crothall |
| 6,056,738 A | 5/2000 | Marchitto et al. |
| 6,057,925 A | 5/2000 | Anthon |
| 6,061,581 A | 5/2000 | Alam et al. |
| 6,061,582 A | 5/2000 | Small et al. |
| 6,063,039 A * | 5/2000 | Cunningham et al. ...... 600/573 |
| 6,070,093 A | 5/2000 | Oosta et al. |
| 6,073,037 A | 6/2000 | Alam et al. |
| 6,078,042 A | 6/2000 | Fellows |
| 6,088,605 A | 7/2000 | Griffith et al. |
| 6,100,811 A | 8/2000 | Hsu et al. |
| 6,115,673 A | 9/2000 | Malin et al. |
| 6,141,101 A | 10/2000 | Bleier et al. |
| 6,146,897 A | 11/2000 | Cohenford et al. |
| 6,147,749 A | 11/2000 | Kubo et al. |
| 6,152,876 A | 11/2000 | Robinson et al. |
| 6,157,041 A * | 12/2000 | Thomas et al. ............... 250/573 |
| 6,172,743 B1 | 1/2001 | Kley et al. |
| 6,175,407 B1 | 1/2001 | Sartor |
| 6,192,261 B1 | 2/2001 | Gratton et al. |
| 6,212,424 B1 | 4/2001 | Robinson |
| 6,224,969 B1 | 5/2001 | Steenbergen et al. |
| 6,226,541 B1 | 5/2001 | Eppstein et al. |

| | | | |
|---|---|---|---|
| 6,230,034 B1 | 5/2001 | Messerschmidt et al. | |
| 6,236,047 B1 | 5/2001 | Malin et al. | |
| 6,240,306 B1 | 5/2001 | Rohrscheib et al. | |
| 6,241,663 B1 | 6/2001 | Wu et al. | |
| 6,272,367 B1 | 8/2001 | Chance | |
| 6,280,381 B1 | 8/2001 | Malin et al. | |
| 6,309,884 B1 | 10/2001 | Cooper et al. | |
| 6,441,388 B1 | 8/2002 | Thomas et al. | |
| 6,558,320 B1 * | 5/2003 | Causey et al. | 600/300 |
| 6,866,675 B1 * | 3/2005 | Perez et al. | 606/181 |
| 2002/0171834 A1 | 11/2002 | Rowe et al. | |
| 2003/0007147 A1 | 1/2003 | Johnson | |
| 2003/0023152 A1 | 1/2003 | Abbink et al. | |
| 2003/0023170 A1 | 1/2003 | Gardner et al. | |

FOREIGN PATENT DOCUMENTS

| | | |
|---|---|---|
| EP | 0 449 335 A2 | 10/1991 |
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 757 243 A1 | 2/1997 |
| EP | 0 788 000 A2 | 8/1997 |
| EP | 0 801 297 A1 | 10/1997 |
| EP | 0 836 083 A1 | 4/1998 |
| EP | 0 843 986 A2 | 5/1998 |
| EP | 0 869 348 A2 | 10/1998 |
| EP | 0 897 691 A2 | 2/1999 |
| EP | 0 898 934 A1 | 3/1999 |
| EP | 0 317 121 A2 | 5/1999 |
| EP | 0 982 583 A1 | 3/2000 |
| EP | 0 990 945 A1 | 4/2000 |
| JP | 2000-131143 | 5/2000 |
| JP | 2001-21489 | 1/2001 |
| WO | WO 86/00406 A1 | 1/1986 |
| WO | WO 92/00513 | 1/1992 |
| WO | WO 92/17765 | 10/1992 |
| WO | WO 93/00855 | 1/1993 |
| WO | WO 93/07801 | 4/1993 |
| WO | WO 95/22046 | 8/1995 |
| WO | WO 97/23159 | 7/1997 |
| WO | WO 97/27800 | 8/1997 |
| WO | WO 97/28437 | 8/1997 |
| WO | WO 97/28438 | 8/1997 |
| WO | WO 98/01071 | 1/1998 |
| WO | WO 98/37805 | 9/1998 |
| WO | WO 98/40723 | 9/1998 |
| WO | WO 99/09395 | 2/1999 |
| WO | WO 99/37203 | 7/1999 |
| WO | WO 99/43255 | 9/1999 |
| WO | WO 99/46731 | 9/1999 |
| WO | WO 99/55222 | 11/1999 |
| WO | WO 99/56616 | 11/1999 |
| WO | WO 00/24454 A1 | 5/2000 |
| WO | WO 00/65988 A1 | 11/2000 |
| WO | WO 01/15596 | 3/2001 |
| WO | WO 01/16579 A1 | 3/2001 |
| WO | WO 01/18543 A1 | 3/2001 |
| WO | WO 01/28417 A1 | 4/2001 |
| WO | WO 01/58344 A1 | 8/2001 |
| WO | WO 02/065090 A2 | 8/2002 |
| WO | WO 02/082989 A1 | 10/2002 |

OTHER PUBLICATIONS

Aussedat et al., "Interstitial Glucose Concentration and Glycemia: Implications for Continuous Subcutaneous Glucose Monitoring," *Am J. Physiol. Endocrinol Metab.*, vol. 278, No. 4, Apr. 2000, 22 pages.

Anderson, C.E. et al., "Fundamentals of Calibration Transfer Through Procrustes Analysis," *Appln. Spectros.*, vol. 53, No. 10 (1999) p. 1268.

Anderson, Robert J. et al., "Errors in Absorbance Measurements in Infrared Fourier Transform Spectrometry because of Limited Instrument Resolution," *Analytical Chemistry*, vol. 47, No. 14, Dec. 1975, pp. 2339-2347.

Anderson, Robert J. et al., "Resolution and Instrument Line Shape Effects on Spectral Compensation with Fourier Transform Infrared Spectrometers," *Analytical Chemistry*, vol. 50, No. 13, Nov. 1978, pp. 1804-1811.

Ashbourn, Julian, *Biometrics: Advanced Identity Verification*, Springer, 2000, pp. 63-64.

Atherton, P.D. et al., "Tunable Fabry-Perot Filters," *Optical Engineering*, vol. 20, No. 6, Nov./Dec. 1981, pp. 806-814.

Bantle, John P. et al., "Glucose Measurement in Patients with Diabetes Mellitus with Dermal Interstitial Fluid," *J. Lab Clin Med.*, vol. 130, No. 4, Oct. 1997, pp. 436-441.

Beebe, Kenneth R. et al., "Chapter 3: Preprocessing," *Chemometrics: A Practical Guide*, ©John Wiley & Sons, Inc., date unknown, pp. 26-55.

Blank, T.B. et al., "Transfer of Near-Infrared Multivariate Calibrations Without Standards," *Anal. Chem.*, vol. 68 (1996) p. 2987.

Brasunas John C. et al., "Uniform Time-Sampling Fourier Transform Spectroscopy," *Applied Optics*, vol. 36, No. 10, Apr. 1, 1997, pp. 2206-2210.

Brault, James W., "New Approach to High-Precision Fourier Transform Spectrometer Design," *Applied Optics*, Vo. 35, No. 16, Jun. 1, 1996, pp. 2891-2896.

Breiman, Leo, "Bagging Predictors," *Machine Learning*, vol. 24 (1996) pp. 123-140.

Cassarly, W.J. et al., "Distributed Lighting Systems: Uniform Light Delivery," *Source Unknown*, pp. 1698-1702.

Chang, Chong-Min et al., "An Uniform Rectangular Illuminating Optical System for Liquid Crystal Light Valve Projectors," *Euro Display '96* (1996) pp. 257-260.

Coyne, Lawrence J. et al., "Distributive Fiber Optic couplers Using Rectangular Lightguides as Mixing Elements," (Information Gatekeepers, Inc. Brookline, MA, 1979) pp. 160-164.

de Noord, Onno E., "Multivariate Calibration Standardization," *Chemometrics and Intelligent Laboratory Systems 25*, (1994) pp. 85-97.

Despain, Alvin M. et al., "A Large-Aperture Field-Widened Interferometer-Spectrometer for Airglow Studies," Aspen International Conference on Fourier Spectroscopy, 1970, pp. 293-300.

Faber, Nicolaas, "Multivariate Sensitivity for the Interpretation of the Effect of Spectral Pretreatment Methods on Near-Infrared Calibration Model Predictions," *Analytical Chemistry*, vol. 71, No. 3, Feb. 1, 1999, pp. 557-565.

Gabriely, Ilan MD et al., "Transcutaneous Glucose Measurement Using Near-Infrared Spectroscopy During Hypoglycemia," *Diabetes Care*, vol. 22, No. 12, Dec. 1999, pp. 2026-2032.

Geladi, Paul et al., "A Multivariate NIR Study of Skin Alterations in Diabetic Patients as Compared to Control Subjects," *J. Nera Infrared Spectrosc.*, vol. 8 (2000) pp. 217-227.

Haaland, David M., "Multivariate Calibration Methods Applied to the Quantitative Analysis of Infrared Spectra," *Computer-Enhanced Analytical Spectroscopy*, vol. 3 (1992), pp. 1-29.

Haaland, David M. et al. "Reagentless Near-Infrared Determination of Glucose in Whole Blood Using Multivariate Calibration," *Applied Spectroscopy*, vol. 46, No. 10 (1992) pp. 1575-1578.

Harwit, M. et al., "Chapter 5—Instrumental Considerations" *Hadamard Transform Optics*, Academic Press (1979) pp. 109-145.

Hazen, Kevin H. et al., "Measurement of Glucose and Other Analytes in Undiluted Human Serum with Near-Infrared Transmission Spectroscopy, " *Analytica Chemica Acta*, 371 (1998) 255-267.

Heinemann, Lutz et al., "Continuous Glucose Monitoring: An Overview of Today's Technologies and Their Clinical Applications," *IJCP Supplement 129*, Jul. 2002, pp. 75-79.

Heise H. Michael et al., "Near-Infrared Reflectance Spectroscopy for Noninvasive Monitoring of Metabolites," *Clin. Chem. Lab. Med. 2000*, 38(2) (2000) pp. 137-145.

Heise, H.M. "Non-Invasive Monitoring of Metabolites Using Near Infrared Spectroscopy: State of the Art," *Horm. Metab. Res.*, vol. 28 (1996) pp. 527-534.

Heise, H.M. et al., "Near Infrared Spectrometric Investigation of Pulsatile Blood Flow for Non-Invasive Metabolite Monitoring," *CP430, Fourier Tranform Spectroscopy: 11th International Conference*, (1998) pp. 282-285.

Heise, H.M. et al., "Noninvasive Blood Glucose Sensors Based on Near-Intrared Spectroscopy," *Artif Organs*, vol. 18, No. 6 (1994) pp. 1-9.

Herbel et al., "Hypoglycemia Pathophysiology and Treatment," *Endocrinology and Metabolism Clinics*, vol. 29, No. 4, Dec. 2000, 16 pages.

Hopkins, George W. et al., "In-vivo NIR Diffuse-reflectance Tissue Spectroscopy of Human Subjects," *SPIE*, vol. 3597, Jan. 1999, pp. 632-641.

Jagemann, Kay-Uwe et al. "Application of Near-Infrared Spectroscopy for Non-Invasive Determination of Blood/Tissue Glucose Using Neural Networks," *Zeitschrift for Physikalische Chemie*, Bd.191, S. 179-190 (1995).

Johansen, Ib-Rune et al., "Calibration of an FT-IR Spectrometer for Ambient Air Monitoring Using PLS," *Applied Spectroscopy*, vol. 51, No. 10 (1997,) pp. 1540-1546.

Khalil, Omar S., "Spectroscopic and Clinical Aspects of Noninvasive Glucose Measurements," *Clinical Chemistry*, 45:2 (1999) pp. 165-177.

Kohl, Matthias et al., "Influence of Glucose concentration on Light Scattering in Tissue-Simulating Phantoms," *Optics Letters*, vol. 19, No. 24, Dec. 15, 1994, pp. 2170-2172.

Kohl, Matthias et al., "The Influence of Glucose Concentration Upon the Transport of Light in Tissue-simulating Phantoms," *Phys. Med. Biol.*, vol. 40 (1995) pp. 1267-1287.

Korte, E.H. et al., "Infrared Diffuse Reflectance Accessory for Local Analysis on Bulky Samples," *Applied Spectroscopy*, vol. 42, No. 1, Jan. 1988, pp. 38-43.

Kumar, G. et al., "Optimal Probe Geometry for Near-Infrared Spectroscopy of Biological Tissue," *Applied Spectroscopy*, vol. 36 (1997) p. 2286.

Kuwa, Katsuhiko et al. "Relationships of Glucose Concentrations in Capillary Whole Blood, Venous Whole Blood and Venous Plasma," *Clinica Chimica Acta*, 307 (3001) pp. 187-192.

Lorber, Avraham et al., "Local Centering in Multivariate Calibration," *Journal of Chemometrics*, vol. 10 (1996) pp. 215-220.

Lorber, Avraham et al., "Net Analyte Signal Calculation in Multivariate Calibration," *Analytical Chemistry*, vol. 69, No. 8, Apr. 15, 1997, pp. 1620-1626.

Malin, Stephen F., "Non-Invasive Measurement of Glucose by Near Infrared Diffuse Reflectance Spectroscopy," *31st Annual Oak Ridge Conference*, Sigma Diagnostics, Inc., Apr. 23, 1999, 1 sheet.

Manasteriski, A. et al. "Blanking and the Determination of Cholesterol," *Mikrochimica Acta*, (1975 II) pp. 1-16.

Marbach, R. et al, "Noninvasive Blood Glucose Assay by Near-Infrared Diffuse Reflectance Spectroscopy of the Human Inner Lip," *Applied Spectroscopy*, vol. 47, No. 7 (1993) pp. 875-881.

Marbach, R. et al. "Optical Diffuse Reflectance Accessory for Measurements of Skin Tissue by Near-Infrared Spectroscopy," *Applied Optics*, vol. 34, No. 4, Feb. 1, 1995, pp. 610-621.

Marbach, Ralf, "Measurement Techniques for IR Spectroscopic Blood Glucose Determination," (1994) pp. 1-158.

Mardia, K.V. et al., *Multivariate Analysis*, Academic Press (1979) pp. 300-325.

Martens, Harald et al., Updating Multivariate Calibrations of Process NIR Instruments, *Adv. Instru. Control*(1990) pp. 371-381.

McGarraugh, Geoff et al., "Glucose Measurements Using Blood Extracted from the Forearm and the Finger,"©TheraSense, Inc. (2001) pp. 1-7.

McGuire E.A.H. et al., "Effects of Arterial Versus Venous Sampling on Analysis of Glucose Kinetics in Man," *Journal of Applied Physiology*, vol. 41, No. 4, Oct. 1976, pp. 565-572.

McIntosh, Bruce C. et al. "Quantitative Reflectance Spectroscopy in the Mid-IR, *16th Annual FACSS Conference*, Oct. 1989.

Monfre, Stephen L. et al., "Physiologic Differences Between Volar and Dorsal Capillary Forearm Glucose Concentrations and Finger Stick Glucose Concentrations in Diabetics," *Abstracts from the ADA 62nd Scientific Sessions*, date unknown, p. A125, No. 503-P. (abstract).

Nichols, et al., *Design and Testing of a White-Light, Steady-State Diffuse Reflectance Spectrometer for Determination of Optical Properties of Highly Scattering Systems*, Applied Optics, Jan. 1, 1997, 36(1), pp. 93-104.

Offner, A., "New Concepts in Projection Mask Aligners," *Optical Engineering*, vol. 14, No. 2, Mar.-Apr. 1975, pp. 130-132.

Osborne, B.G. et al., "Optical Matching of Near Infrared Reflectance Monochromator Instruments for the Analysis of Ground and Whole Wheat," *J. Near Infrared Spectrosc.*, vol. 7 (1999) p. 167.

Ozdemir, d. et al., "Hybrid Calibration Models: An Alternative to Calibration Transfer,"0 *Appl. Spectros,*, vol. 52, No. 4 (1998) p. 599.

Powell, J.R. et al, "An Algorithm for the Reproducible Spectral Subtraction of Water from the FT-IR Spectra of Proteins in Dilute Solutions and Adsorbed Monolayers," *Applied Spectroscopy*, vol. 40, No. 3 (1986) pp. 339-344.

Ripley, B.D. *Pattern Recognition and Neural Networks*, Cambridge University Press (1996) pp. 91-120.

Robinson, M. Ries et al., "Noninvasive Glucose Monitoring in Diabetic Patients: A Preliminary Evaluation," *Clinical Chemistry*, vol. 38, No. 9 (1992) pp. 1618-1622.

Royston, David D. et al., "Optical Properties of Scattering and Absorbing Materials Used in the Development of Optical Phantoms at 1064 NM," *Journal of Biomedical Optics*, vol. 1, No. 1, Jan. 1996, pp. 110-116.

Rutan, Sarah C. et al., "Correction for Drift in Multivariate Systems Using the Kalman Filter," *Chemometrics and Intelligent Laboratory Systems 35*, (1996) pp. 199-211.

Salit, M.L. et al., "Heuristic and Statistical Algorithms for Automated Emission Spectral Background Intensity Estimation," *Applied Spectroscopy*, vol. 48, No. 8 (1994) pp. 915-925.

Saptari, Vidi Alfandi, "Analysis Design and Use of a Fourier-Transform Spectrometer for Near Infrared Glucose Absorption Measurement,"(Massachusetts Institute of Technology, 1999) pp. 1-76.

Schmitt, J.M. et al., "Spectral Distortions in Near-Infrared Spectroscopy of Turbid Materials," *Applied Spectroscopy*, No. 50 (1996) p. 1066.

Service, F. John et al., Dermal Interstitial Glucose as an Indicator of Ambient Glycemia, *Diabetes Care*, vol. 20, No. 9, Sep. 1997, 9 pages.

Shroder, Robert, (Internet Article) MicroPac Forum Presentation, Current performance results, May 11, 2000.

Sjoblom, J. et al., "An Evaluation of Orthogonal Signal correction Applied to Calibration Transfer of Near Infrared Spectra," *Chemom & Intell Lab. Sys.*, vol. 44 (1998) p. 229.

Spitz, Henry et al., "A New Anthropometric Phantom for Calibrating In Vivo Measurements of Stable Lead in the Human Leg Using X-ray Fluorescence," *Health Physics*, vol. 78, No. 2, Feb. 2000, pp. 159-169.

Steel, W.H., "Interferometers for Fourier Spectroscopy," Aspen International Conference on Fourier Spectroscopy, (1970) pp. 43-53.

Sternberg R.S. et al., "A New Type of Michelson Interference Spectrometer,"*Sci. Instrum.*, vol. 41 (1964) pp. 225-226.

Stork, Chris L. et al., "Weighting Schemes for Updating Regression Models—a Theoretical Approach," *Chemometrics and Intelligent Laboratory Systems 48*, (1999) pp. 151-166.

Sum, Stephen T. et al., "Standardization of Fiber-Optic Probes for Near-Infrared Multivariate Calibrations,"*Applied Spectroscopy*, vol. 52, No. 6 (1998) pp. 869-877.

Swierenga, H. et al., "Comparison of Two Different Approaches Toward Model Transferability in NIR Spectroscopy," *Applied Spectroscopy*, vol. 52, No. 1 (1998) pp. 7-16.

Swierenga, H. et al., "Improvement of PLS Model Transferability by Robust Wavelength Selection," *Chemometrics and Intelligent Laboratory Systems*, vol. 41 (1998) pp. 237-248.

Swierenga, H. et al., "Strategy for Constructing Robust Multivariate Calibration Models," *Chemometrics and Intelligent Laboratory Systems*, vol. 49 (1999) pp. 1-17.

Teijido, J.M. et al., "Design of a Non-conventional Illumination System Using a Scattering Light Pipe," *SPIE*, vo. 2774 (1996) pp. 747-756.

Teijido, J.M. et al., "Illumination Light Pipe Using Micro-Optics as Diffuser," *SPIE*, vol. 2951 (1996) pp. 146-155.

Thomas, Edward V. et al., "Development of Robust Multivariate Calibration Models," *Technometrics*, vol. 42, No. 2, May 2000, pp. 168-177.

Tipler, Paul A., *Physics, Second Edition*, Worth Publishers, Inc., Chapter 34, Section 34-2, Nov. 1983, pp. 901-908.

Wang, Y-D. et al., "Calibration Transfer and Measurement Stability of Near-Infrared Spectrometers," *Appl. Spectros.*, vol. 46, No. 5 (1992) pp. 764-771.

Wang, Y-D. et al., "Improvement of Multivariate Calibration Through Instrument Standardization," *Anal. Chem.*, vol. 64 (1992) pp. 562-564.

Wang, Z., "Additive Background Correction in Multivariate Instrument Standardization," *Anal. Chem.*, vol. 67 (1995) pp. 2379-2385.

Ward, Kenneth J. et al., "Post-Prandial Blood Glucose Determination by Quantitative Mid-Infrared Spectroscopy," *Applied Spectroscopy*, vol. 46, No. 6 (1992) pp. 959-965.

Webb, Paul, "Temperatures of Skin, Subcutaneous Tissue, Muscle and Core in Resting Men in Cold, Comfortable and Hot Conditions," *European Journal of Applied Physiology*, vol. 64(1992) pp. 471-476.

Whitehead, L.A. et al., "High-efficiency Prism Light Guides with Confocal Parabolic Cross Sections," *Applied Optics*, vol. 37, No. 22 (1998) pp. 5227-5233.

\* cited by examiner

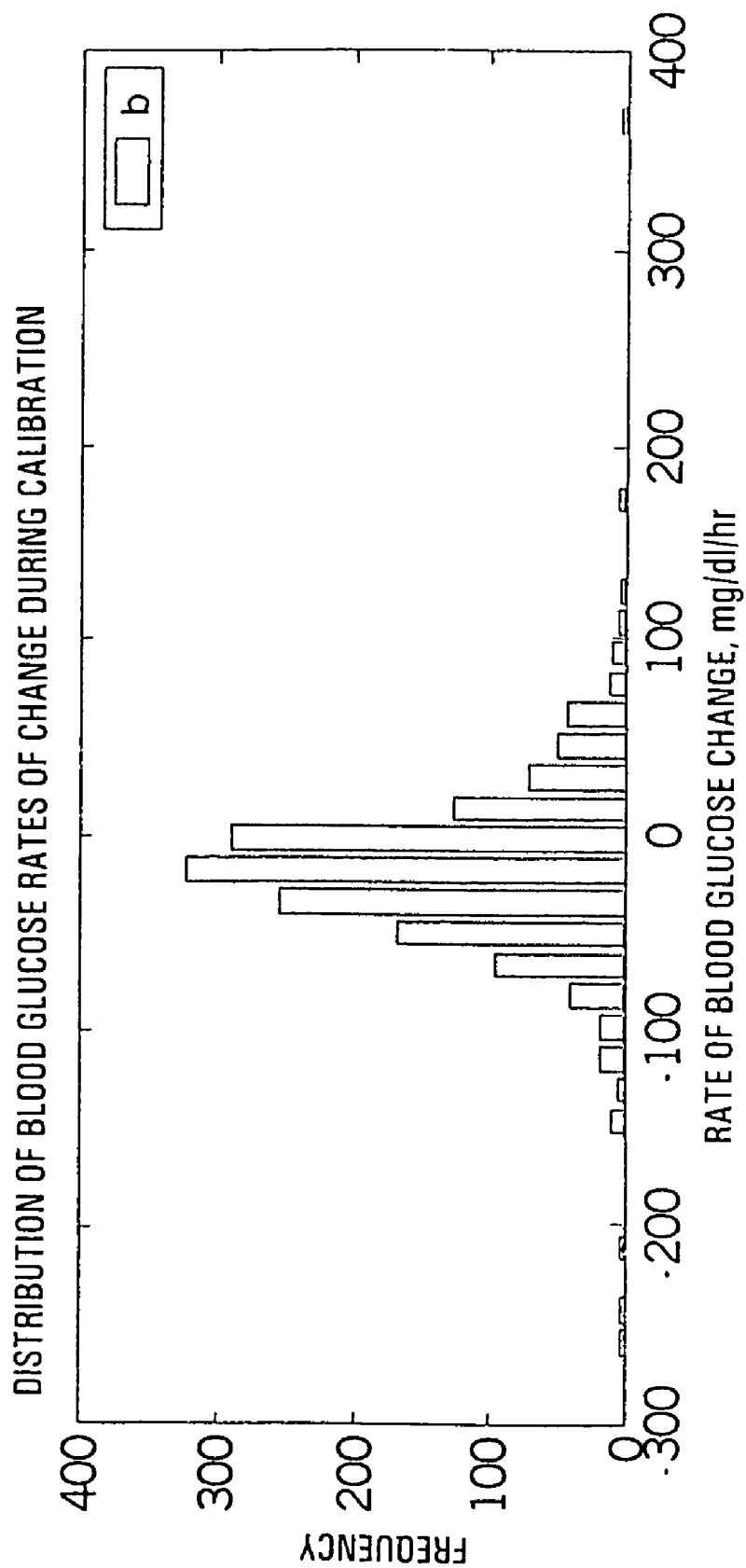

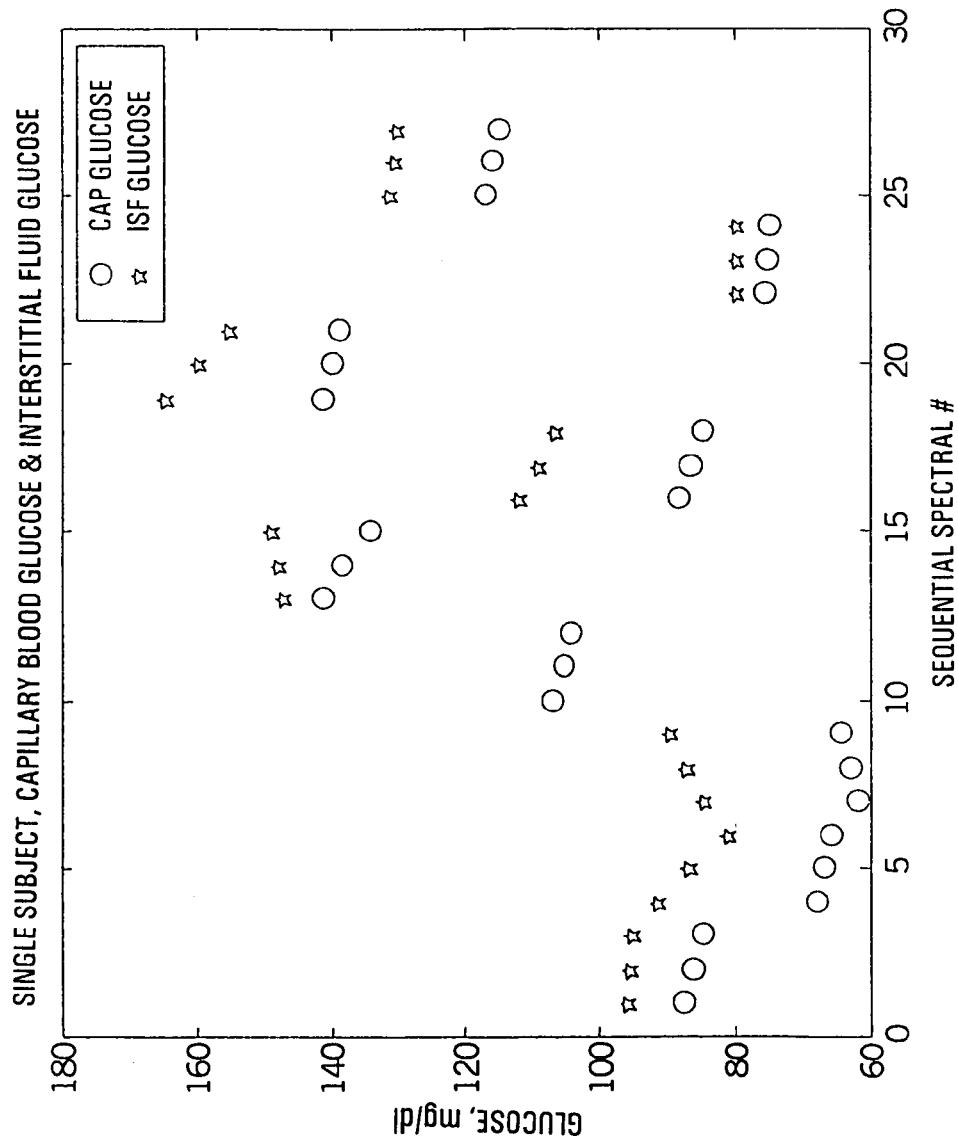

APPARATUS AND METHOD FOR NON-INVASIVE SPECTROSCOPIC MEASUREMENT OF ANALYTES IN TISSUE USING A MATCHED REFERENCE ANALYTE

RELATED APPLICATIONS

This application is related to U.S. patent application Ser. No. 09/832,585, entitled "System for Non-Invasive Measurement of Glucose in Humans"; U.S. patent application Ser. No. 09/832,586, entitled "Illumination Device and Method for Spectroscopic Analysis"; U.S. patent application Ser. No. 09/832,631, entitled "Encoded Variable Filter Spectrometer"; and U.S. patent application Ser. No. 09/832,608, entitled "Optically Similar References Samples and Related Methods for Multivariate Calibration Models Used in Optical Spectroscopy", all filed on Apr. 11, 2001, and assigned to the assignee of the present application. The disclosure of each of these related applications is hereby incorporated by reference.

TECHNICAL FIELD

The present invention generally relates to a quantitative spectroscopy system for measuring analyte concentrations or other attributes of tissue utilizing non-invasive techniques in combination with multivariate analysis. More specifically, the present invention relates to a method for building improved calibration models which uses a matched analyte reference measurement to ensure that the correct relationship between the spectra and reference measurement of the analyte is made during the calibration process and a system incorporating the developed calibration model.

BACKGROUND OF THE INVENTION

The need for an accurate and non-invasive method for determining attributes of or analyte concentrations in bodily tissues, bodily fluids or other biological samples is well documented. For example, accurate non-invasive measurement of blood glucose levels in diabetic patients would greatly improve diabetes treatment. U.S. Pat. No. 5,379,764 to Barnes et al. discloses the necessity for diabetics to frequently monitor blood glucose levels. The more frequent the blood glucose levels are measured, the less likely the occurrence of large swings in blood glucose levels. These large swings are associated with the very undesirable short-term symptoms and long-term complications of diabetes. Such long-term complications include heart disease, arteriosclerosis, blindness, stroke, hypertension, kidney failure, and premature death.

Several systems have been proposed for the non-invasive measurement of blood glucose levels. However, despite these efforts, direct and invasive measurements (e.g., blood sampling by a lancet cut into the finger) are still necessary for most if not all presently FDA approved and commercially available glucose monitors. This is believed so compromising to the diabetic patient that frequent blood glucose measurement, which is necessary to ensure effective diabetes management, is rarely achieved.

It has been recognized that when the body is measured non-invasively, various parts of the body may be interrogated, such as the skin, the eye, the finger, etc. Also, depending on the non-invasive technique in question, different fluid compartments within the body may be measured. For example, European Patent No. 0 757 243 states that, "reflective arm measurements are limited to capillary blood (and interstitial fluid) almost exclusively". Thennadil et al. (2001) also state that, "the glucose "seen" by the light consists of glucose in both the ISF and the capillary blood." European Patent No. 0 631 137 states "the spectral information utilized by these methods includes not only that generated by glucose in the blood but also that from glucose in the interstitial fluid and other tissues." Furthermore, International Publication No. WO 99/43255 reports that, "when light passes through the tongue it is believed that the majority of the photons will interact with interstitial fluid not blood."

Since the advent of non-invasive blood glucose monitoring, many have reported using invasive finger capillary blood measurements as references, including Heise et al. in "Near-Infrared Reflectance Spectroscopy for Noninvasive Monitoring of Metabolites" (Clin. Chem. Lab. Med. 2000) and Ward et al. (1992). No distinction has been made about the best time to collect these reference measurements. Ward et al. actually reported using these references post-prandially, when the difference between capillary glucose and interstitial glucose can be expected to be at its greatest. Plasma glucose readings have also been used as calibration standards as stated by Gabriely et al. in "Transcutaneous Glucose Measurement Using Near-Infrared Spectroscopy During Hypoglycemia" (The American Diabetes Association, Inc., 1999), where the blood in question was venous blood. Venous readings are impractical outside of the process of calibration, for example, in cases where a home-user would make invasive measurements as a quality check or as part of a calibration model-updating scheme.

Using blood glucose as a reference for non-invasive measurements has been reported in published patent applications, such as International Publication No. WO 98/37805, where it is stated, "the patient's blood glucose is measured with a highly accurate invasive method which is relied upon to yield a reference measurement of the patient's blood glucose". International Publication No. WO 01/16579 states that, "this individual calibration process requires taking a number of blood samples over a period of time from the individual, and obtaining reference glucose concentration measurements from these samples", while International Publication No. WO 01/09589 reports that, "the glucose meter commercially available for diabetics' self use can be used to measure glucose concentration in the blood from a few microliters of capillary blood obtained, e.g., by lancing a finger."

It is clear that while several researchers have acknowledged the fact that glucose kinetics result in differences between glucose in different compartments, there seems to be differing opinions on the extent to which the differences occur. For example, McGarraugh et al. in "Glucose Measurements Using Blood Extracted from the Forearm and the Finger" (Therasense White Paper, 2001) note that "changes in blood glucose are first detected in the finger sample and the changes lag in the arm measurements", and that "glucose concentration from the arm never reaches as high a peak as the finger, nor does it experience as low a valley". They concluded that, "the extremes in glucose readings from finger capillaries tend to be damped in capillary blood from the arm"

In addition, U.S. Pat. No. 6,049,727 to Crothall states that, "it is known that glucose levels in interstitial fluid lag glucose levels in blood by about 20 minutes." Kuwa et al. in "Relationships of Glucose concentrations in Capillary Whole Blood, Venous Whole Blood and Venous Plasma" (Clin. Chim. Acta., 2001), also report that "post-loaded glucose values in capillary blood were significantly higher than those in venous blood", and said that the reason for the difference was glucose consumption in the tissues. Meanwhile, McGuire et al. in "Effects of Arterial Versus Venous Sampling on Analysis of Glucose Kinetics in Man" (J. Appl. Phys., 1976) state that the reason for the difference in glucose concentration between arterial and venous blood was, "(1) the transit times of substances through the circulatory paths between the two sampling sites, and (2) the loss of substances to the intervening tissues". On the other hand, International Publication No. WO 01/18543 states that, "although there is a time lag of a few minutes before changes in blood glucose concentration are reflected in the interstitial fluid, this lag is negligible compared to the usual time between measurements . . . measurement of interstitial fluid glucose may be an adequate surrogate for measurement of capillary blood glucose". This opinion is also shared by Thennadil et al. (2001), who state, "no observable lag among ISF, and capillary and venous plasma glucose levels when blood glucose levels change rapidly". This is contrary to International Publication No. WO 01/47408, whose authors have developed a "system for determining the level of glucose of a user, comprising a sampling device used to take a sample of interstitial fluid (ISF) and a means for reducing the time lag between the concentration of glucose in interstitial fluid and in the blood of the patient." Thennadil et al. (2001), commenting on a non-invasive glucose calibration model generated using finger capillary blood glucose as a reference, say that, "any difference in glucose levels between the ISF and capillary blood will lead to a 'reference' error, which will depend on the relationship between blood and ISF glucose concentrations. If this 'reference' error is large, then the error in the non-invasive estimation of glucose will be dominated by it". As mentioned above, however, they go on to conclude that there is, "no observable lag among ISF, and capillary and venous plasma glucose levels when blood glucose levels change rapidly."

SUMMARY OF THE INVENTION

When research into non-invasive meters began, the obvious glucose reference method to use in calibrating and validating the instruments was finger capillary glucose determination, which was the method approved by the FDA for commercially available glucose monitors. However, it has been found and the present invention addresses the finding that finger capillary glucose is not the best reference for non-invasive measurements in many applications, as disclosed in detail below. The present invention incorporates a matched reference, the form of which can vary depending on the circumstance of the measurement. Generally, in preferred embodiments, the best reference will measure analyte concentration from the same sample that is interrogated by the non-invasive measurement. While this invention is appropriate for any body analyte or tissue characteristic, it is particularly applicable to glucose, since glucose kinetics may sometimes cause glucose to be present in different concentrations in different tissues in the body. For example, the reference that is used for a glucose near infrared (NIR) non-invasive measurement in preferred embodiments is dermal interstitial fluid glucose concentration. This is due to a finding that most of the glucose that is "seen" by the NIR of the present invention in the interrogated sample is in the interstitial fluid space. This interstitial, dispersed body fluid exists in the interstitial space defined between collagen fibers and cells in the skin's connective tissue, and includes constituents such as glucose. It is believed to contain few or no red blood cells.

Due to the various physiological conditions that can cause the interstitial fluid glucose to mirror other compartments at some times but not at others, this invention allows for different reference measurements, depending on the particular occasion. If blood glucose monitoring measurements are taken before a meal or before bed in order to determine the proper insulin dosage, the blood glucose is least likely to be in rapid transition. The blood glucose should not be rising rapidly from recent ingestion of carbohydrates, nor should it be falling rapidly from administered insulin. This is the physiological condition when the difference between glucose concentration at the finger and the arm is at a minimum. At such a time, therefore, it would be appropriate in an embodiment of the present invention to choose any compartment as a reference for the non-invasive measurement. Other techniques such as heating or rubbing a sample site or applying a vasodilating agent can also result in situations where different compartments will have similar glucose or other analyte concentrations so that time and location may define alternative satisfactory reference samples.

In preferred embodiments of the present invention, methods incorporating a matched reference sample can be utilized to modify an existing calibration model in the non-invasive spectroscopic measurement of an analyte or attribute of tissue. Alternatively, the matched reference sample can be utilized to perform subject-specific modifications in a non-invasive spectroscopic measurement of an analyte or attribute of tissue. Matched reference samples can also be utilized in a preferred method for building a calibration model for non-invasive spectroscopic measurement of an analyte or attribute of tissue. In an alternative embodiment, a matched reference sample or samples can be used in a method for measuring a biological attribute in human tissue or it can be utilized to validate non-invasive measurement performance on a non-invasive spectroscopic measurement instrument which is utilized to analyze tissue. Finally, matched reference samples of the present invention can be utilized to correct predictions which are made by non-invasive spectroscopic instruments.

In one preferred method for performing modifications to calibration models, a means for irradiating tissue with infrared energy is provided. Further, an output element which is operatively connected to a means for measuring a spectrum is provided. The tissue is irradiated with the infrared energy so that there is absorption of at least a portion of the infrared energy in the tissue. At least a portion of the infrared energy exiting the tissue through the output element is collected and measured, resulting in a spectrum. At least one matched reference sample is collected and assayed to determine at least one reference value of the analyte or attribute of tissue, and the at least one reference value is used with the spectral measurement to perform a modification to the calibration model.

In one preferred embodiment, the matched reference sample is interstitial fluid and the analyte of interest measured in the spectroscopic measurement is glucose. In an alternative embodiment, the matched reference sample is bulk fluid in the tissue. In some embodiments, the matched reference sample is fluid obtained from a limb or a lancet blood sample obtained from a forearm. In a preferred embodiment, the matched reference sample is a fluid taken from a tissue compartment that is kinetically matched to the tissue which is irradiated. In an alternative embodiment, the matched reference sample is a fluid taken from a tissue compartment that is spatially matched to the fluid containing tissue. In some embodiments, site-to-site variations are reduced through use of multiple collection of matched reference samples of the tissue over a sufficient area. It is preferred that the optically sampled area and area used for procurement of multiple matched reference samples are similar in size.

In alternative embodiments, the reference samples are used to perform subject-specific modifications in a non-invasive spectroscopic measurement of an analyte or attribute of tissue. In one embodiment, the reference samples are kinetically matched to the irradiated tissue and assayed for the analyte or attribute of tissue. The assayed reference samples are used with the spectral measurements to perform a subject-specific modification. In an alternative embodiment, the reference samples collected are spatially matched to the irradiated tissue and assayed for the analyte or attribute of tissue which measurement is then used with the spectral measurements to perform a subject-specific modification.

Alternatively, the reference samples are obtained via multiple samplings from any fluid compartment or combinations of fluid compartments and assayed for use with the spectral measurements to perform the subject-specific modification. In preferred embodiments, the area for collecting multiple reference samples is similar to the area that is irradiated on the tissue.

It is also preferred in some embodiments that the reference measurements use a process that ensures that the difference in analyte concentration between the reference sample fluid compartment and the spectroscopically sample fluid compartment is not clinically significant. In a preferred spectroscopic measurement of glucose in tissue, the reference samples are collected under moderately stable glucose levels, then assayed and used with the spectral measurements to perform a subject-specific modification. When glucose is the analyte of interest, the reference samples can include venous blood, arterial blood, interstitial fluid, capillary blood or mixtures thereof provided they are collected under conditions of moderately stable glucose levels so that the fluid compartments do not vary in a clinically significant way. Equilibration techniques such as heating or use of vasodilating agents can be utilized to achieve a matched reference sample prior to taking the reference sample from the tissue and assaying for the analyte or attribute in tissue.

In one preferred embodiment, however, the reference sample is interstitial fluid when the analyte of interest is glucose. Use of interstitial fluid generally does not require any special procedures to achieve a matched reference sample as the spectroscopic techniques generally include irradiating a tissue sample which is largely made up of interstitial fluid or at least constitutes the bulk fluid in the tissue.

In an alternative method used to build a calibration model for non-invasive spectroscopic measurement of an analyte or attribute of tissue, the above-described apparatus is also utilized. In this method, matched reference samples are collected and assayed for the analyte or attribute of tissue which is to be spectroscopically tested in the future. Spectroscopic data is also collected in conjunction with the matched reference sample data. The reference sample measurements are then used with the infrared measurements to build the multivariate calibration model. In one preferred embodiment, the matched reference sample is interstitial fluid which is particularly useful in building a calibration model for glucose analysis in tissue. The matched reference sample can also be the bulk fluid in the tissue. The matched reference sample can be obtained from a limb or, in one embodiment, lancet blood is obtained from a forearm. In preferred embodiments, the reference sample is from a tissue compartment that is kinetically matched to the non-invasively sampled tissue. It is also preferred that the matched reference sample is from a tissue compartment that is spatially matched to the non-invasively sampled tissue.

Similar techniques are used for measuring a biological attribute in human tissue of a specific subject. Apparatus for measuring infrared absorption which includes an energy source emitting infrared energy in multiple wavelengths is provided. The apparatus includes an input element, an output element and a spectrum analyzer. The input and output elements are coupled to the human tissue, and the tissue is irradiated through the input element with multiple wavelengths of infrared energy with resulting absorption of at least some of those wavelengths. At least a portion of the non-absorbed infrared energy is collected with the output element, followed by determining intensities of the infrared energy. The biological attribute is predicted utilizing a model wherein the subject-specific prediction method uses one or more previously obtained matched reference samples assayed for the biological attribute and one or more previously obtained spectral measurements from the subject. The matched reference samples can include any of those discussed above.

Another preferred embodiment of the present method is used for validating non-invasive measurement performance in a non-invasive spectroscopic measurement system. The above-described apparatus and methods are utilized including the collection of matched reference samples which are assayed for the analyte or attribute of tissue. The matched reference sample measurements, the spectral measurements and a preexisting multivariate calibration model is used to evaluate the non-invasive measurement performance. The preexisting model can contain data from multiple subjects or alternatively from a single subject. The above-disclosed matched reference samples can be utilized.

In an alternative method, the above-described procedures can be utilized in a method for correcting predictions in a non-invasive spectroscopic measurement system. As with the above methods, at least one matched reference sample is collected and assayed for the analyte or attribute of tissue. The result of this test along with the spectral measurements are used to correct future non-invasive analyte predictions.

BRIEF DESCRIPTION OF THE DRAWINGS

FIG. 5 depicts glucose concentrations seen for a single subject from both interstitial fluid measurements and finger capillary blood measurements;

DETAILED DESCRIPTION OF THE PREFERRED EMBODIMENTS

Figure 1:
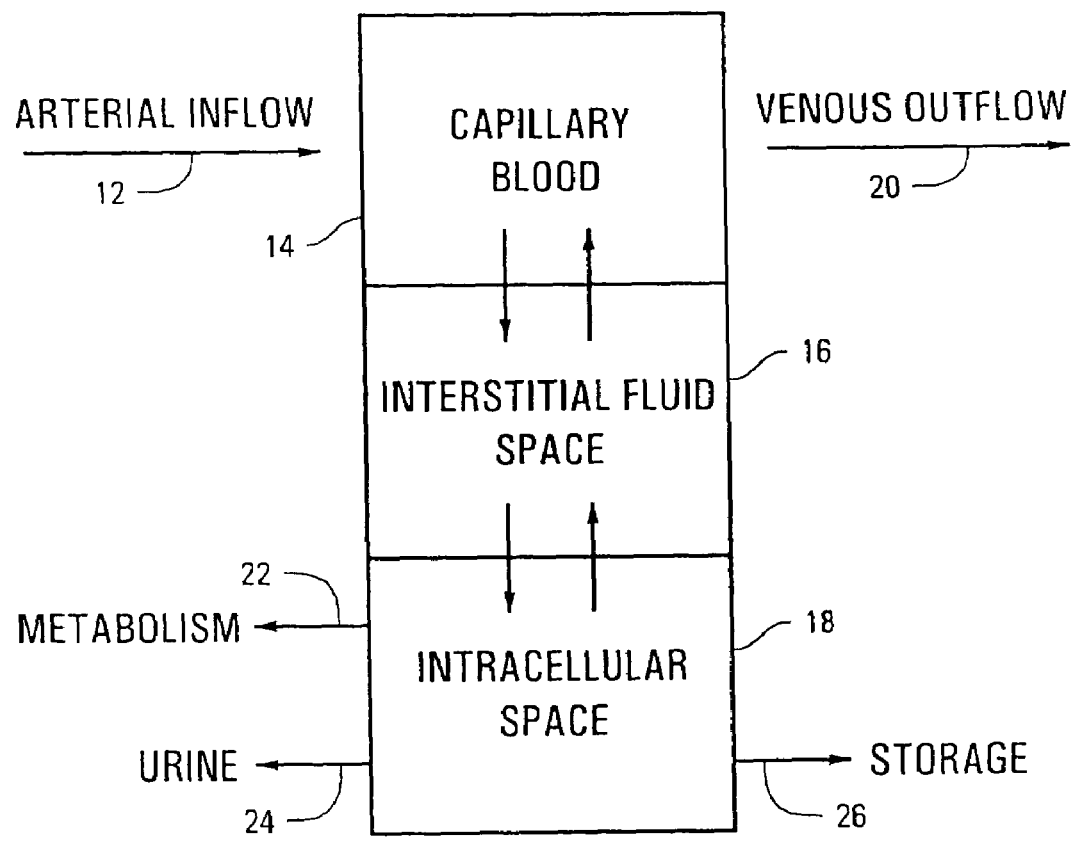
FIG. 1 is a general representation of a tissue compartment that shows glucose transport through the tissue.

In order to understand why different analyte references are appropriate in different circumstances with the present invention, it is necessary to examine the process by which glucose moves through the body, and the kinetics involved. Glucose is essential to all living cells. Sources of glucose include food intake and glycogen breakdown, while sinks include liver, kidney, central nervous system, red blood cells and peripheral tissue. These compartments are linked by blood flow, as illustrated in FIG. 1, which schematically show a tissue section 10. As illustrated, glucose is carried to the various tissues via arterial blood 12, whereupon it passes with the blood into capillaries 14. From there, it diffuses from the capillary blood 14 into the interstitial fluid space 16, and from there into the intracellular space 18. Glucose may be used by the cells through metabolism 22, lost as waste in urine 24 or go to storage 26 such as in proteins. Glucose that has not been used by the cells will diffuse back into the venous blood 20 if the blood glucose concentration is less than the interstitial fluid glucose concentration.

Because diffusion is generally a slow process, glucose transport into and out of the various compartments is not instantaneous. Consequently, the glucose concentration in finger capillary blood is not necessarily the same as the glucose concentration in other compartments such as venous blood or interstitial fluid. The relationship between the concentrations in these compartments depends on the kinetics of the diffusion process.

When glucose levels are rising or falling rapidly, (for example, in response to a meal or an insulin dose) the glucose concentration in the arterial and capillary blood will respond almost instantaneously. The same is true for the brain. The brain has an absolute dependence on glucose and is incapable of storing more than a few minutes of glucose as glycogen. It is the major consumer of glucose in the body in the fasting state. The glucose levels in other compartments will not respond to the stimuli as rapidly, however. The interstitial fluid glucose concentration can lag behind the capillary glucose concentration, and the venous blood glucose concentration can lag it even further. The rate of glucose transfer between compartments depends on physiological factors that vary from person to person and can even vary for a single person. For example, if the air is cold, capillaries near the skin surface will constrict and blood will be shunted away from the skin. In this case, the capillary surface area across which glucose transfer takes place will be severely reduced, the rate of glucose transfer will decrease, and the difference between finger capillary blood glucose and the glucose in other fluid compartments in the body will be exacerbated as blood glucose levels continue to change. Consequently, there are many situations in which the finger capillary glucose concentration will not match the interstitial fluid concentration.

Knowing how the glucose concentration varies from one fluid compartment in the body to another, it has been found that these differences are sufficient to prevent accurate non-invasive measurements, because the calibration of the instrument uses reference measurements different from the non-invasive measurement. For example, the light from NIR spectroscopy used in the present invention penetrates the skin to a depth of ~1 mm; this means that most of the glucose that is "seen" by the NIR light is in the interstitial fluid space, with little glucose information coming from blood. An appropriate glucose reference method for NIR spectral samples, therefore, has been found to be one that measured the glucose concentration in interstitial fluid, not necessarily one that measured the glucose concentration in finger capillary blood. To date, it is believed no one has ever reported using anything other than finger capillary blood glucose (or plasma glucose in a laboratory setting) as a reference for NIR spectroscopy.

Accurate reference glucose measurements are necessary in a number of applications of the present invention. For example, in calibrating a non-invasive instrument, an invasive reference measurement is generally necessary for each spectrum included in the model. If the reference glucose values used to calibrate the instrument are unreliable, then the resulting calibration model will have reduced ability to measure glucose accurately. Another application in which an accurate reference is valuable is in validating the instrument. Validation may take place prior to using the instrument for the first time in the home, but it may also occur on a regular basis in the home to ensure that the instrument is still measuring glucose to a clinically relevant level. In the case of validation, the reference is necessary to verify the accuracy and precision of the non-invasive measurement. A reference that does not match the non-invasive measurement sufficiently will result in incorrect assessments of the accuracy and precision. This is also true in other validation situations, such as in clinical trials where non-invasive instrument performance is being verified. Other applications also exist where accurate reference measurements have been found to be necessary. In any process where reference measurements are collected along with associated spectral measurements for modifications to either the calibration model or to other future spectral measurements, the reference measurement must be accurate in order to effectively perform the modifications.

The present invention provides a method for building improved calibration models, for improving modifications to those models, and for improved validation of the models and the associated non-invasive instruments. The method uses a matched analyte reference measurement to ensure that the correct relationship between the spectra and analyte is made during the calibration process. The matched reference is also essential in later processes that use a spectral measurement and a reference measurement to modify the model.

According to this invention, a matched analyte reference exists when the analyte reference sample concentration or attribute is representative of the analyte concentration or attribute in the site(s) being non-invasively sampled, where the agreement between the reference concentration and the non-invasively sampled concentration is clinically significant. For example, the concentration may be considered representative if the reference measurement is taken from a fluid compartment (or compartments) that is (are) kinetically matched and/or spatially matched to the fluid in the non-invasively sampled tissue, or if the reference fluid represents the bulk of the fluid in the non-invasively sampled tissue. Bulk fluid is the fluid that is present in the largest volume in the non-invasively sampled tissue. It may include blood and/or interstitial fluid.

In the case of non-invasive glucose measurements, a clinically significant level of precision and accuracy is defined as the measurement of glucose concentration in humans to a level of precision and accuracy such that a patient can maintain glycemic control based on the measurement. Glycemic control (controlling the sugar concentration in the body over an extended period) is assessed primarily by periodic measurement of HbA1c levels. Secondary assessment would include regular measurement of both fasting, preprandial and postprandial glucose levels. For preferred embodiments of the present invention, the difference between the reference information and the analyte concentration in the optically sampled tissue is clinically significant if a patient's glycemic control would change if they used the reference glucose information instead of the true analyte concentration in the optically sampled tissue to manage their diabetes.

Figure 13:
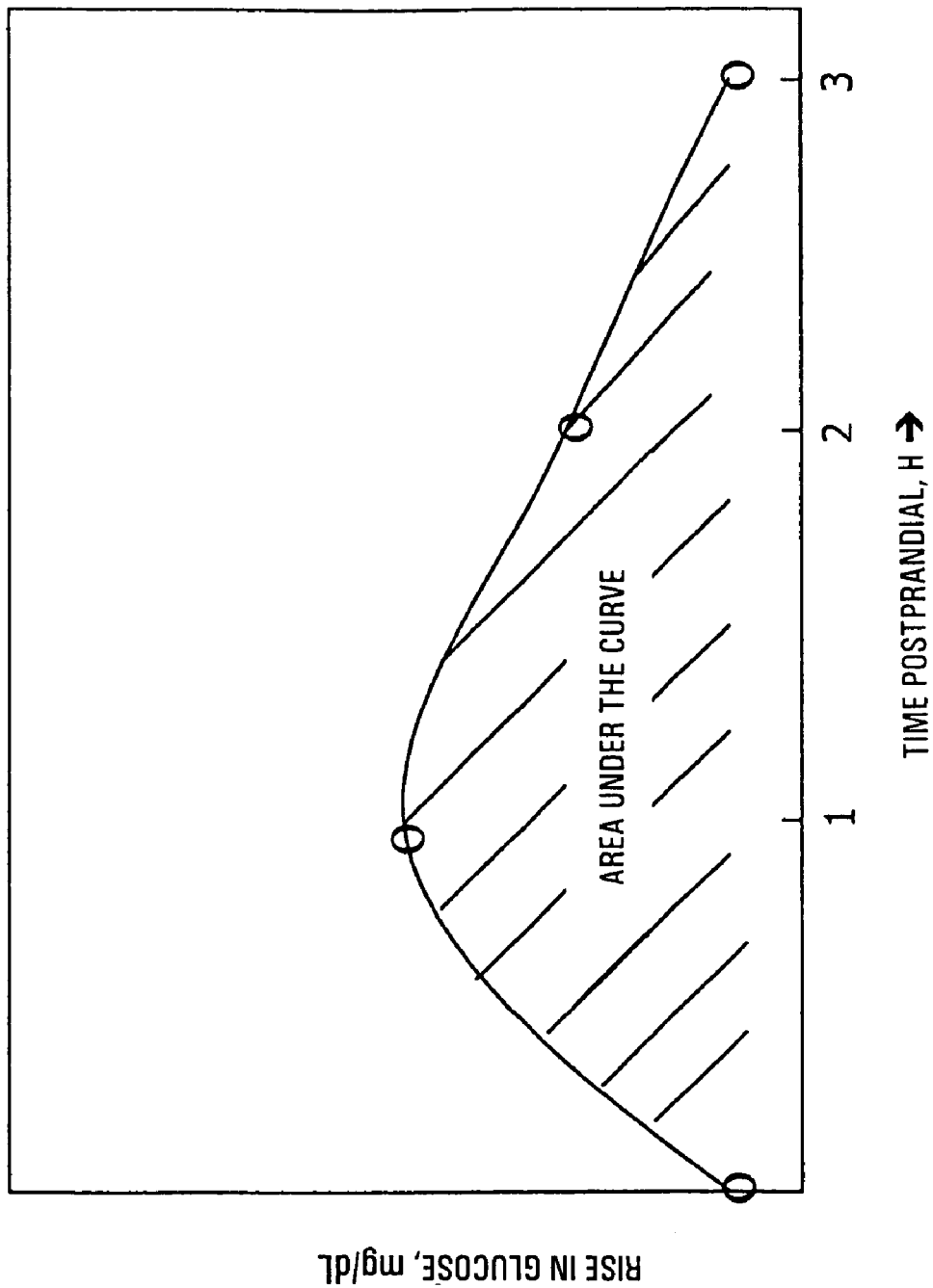
FIG. 13 is a graph depicting one method to determine bioequivalence.

Short term glycemic control can be evaluated in one way using measures of the postprandial rise in glucose, as described by Anderson et al. in "Reduction of Postprandial Hyperglycemia and Frequency of Hypoglycemia in IDDM Patients on Insulin-Analog Treatment" (The American Diabetes Associate, Inc., 1997). This can be used as one means to measure the "bioequivalence" of two methods, which is known to those skilled in the art. In the present case where bioequivalence is used as the standard to determine if a reference is matched to the spectral samples, the glucose is measured at specified intervals following a meal or other glucose load. The area under the curve can then be calculated as depicted in FIG. 13, and this is a measure of the total glucose load during the postprandial period. If this calculation is performed for different reference glucose methods, the area under the curve can be compared with the area under the curve achieved when the analyte concentration in the optically sampled tissue is used. The lower the area under the curve, the better the glucose control. For clinical significance in preferred embodiments, therefore, the reference area under the curve must be close to the non-invasive area under the curve. In representative embodiments, the areas are within 20% of each other, preferably within 10% of each other.

An alternative method to determine clinical significance and whether reference samples are adequately matched uses a Clarke Error Grid, which can be used to display acceptable, preferred and ideal levels of non-invasive glucose measurement precision and accuracy. Table 1 defines these levels in terms of percentage of non-invasive glucose measurements when compared to a reference measurement that fall in the A, B, C, D or E regions of the Clark Error Grid. The bottom line for the glucose measurement is that it must allow the user to effectively maintain glycemic control and avoid either hypo-glycemic or hyper-glycemic conditions. If the Clarke Error grid for the reference measurement versus the non-invasive measurement falls within the percentages listed in Table 1, the agreement is considered to be clinically significant. (The non-invasive glucose measurement is taken to be representative of the true analyte concentration in this case).

TABLE 1

|  | Region A | Region B | Region C | Region D | Region E |
|---|---|---|---|---|---|
| Acceptable | ≧72% | ≦24% | ≦1% | ≦3% | 0% |
| Preferred | ≧85% | ≦14.4% | ≦0.1% | ≦0.5% | 0% |
| Ideal | ≧98.5% | ≦1.5% | 0% | 0% | 0% |

According to the present invention, on any occasion where a reference measurement is taken in association with a spectral measurement, the resulting model or modification will be better if the reference glucose measurement is matched to the spectral glucose measurement. There are many conditions that allow the measurements to be matched. For example, since a NIR spectral measurement interrogates glucose mainly in the interstitial fluid space, but also to a smaller extent, the blood space, the reference measurement should measure, as closely as possible, the glucose that is represented by that spectral glucose measurement. According to the present invention, therefore, a preferred reference for a non-invasive measurement is the measurement of the glucose-containing fluid interrogated by the non-invasive method. For near-infrared measurements, the preferred reference is the measurement of glucose concentration in interstitial fluid. The interstitial fluid sample is best collected close to the site of the non-invasive measurement (for example, from the arm if the non-invasive measurement is at the arm), but interstitial fluid from all body sites will have similar glucose concentrations, so that any interstitial fluid glucose measurement can be a preferred reference.

At times of high glucose flux, for example following a meal or an insulin dose, glucose will move more quickly into some interstitial fluid spaces than others. The rate of change depends on the capillary density in the local area, for example, if a sample of interstitial fluid is taken close to a capillary, the glucose in that sample will be closer kinetically to the glucose in the capillaries than will a sample taken a distance from a capillary bed. According to preferred embodiments, an analyte reference that is kinetically matched to the non-invasive measurement is an improvement over the prior art. A kinetic match exists when the rate of migration of analyte from blood into the non-invasively sampled fluid compartment(s) is similar to the rate of migration of analyte from blood into the fluid compartment(s) used for the reference measurements.

According to the present invention, an analyte reference that is spatially matched to the non-invasive measurement is an improvement over the prior art. A spatial match is achieved when the analyte distribution in the non-invasively sampled fluid compartment(s) is similar to that in the fluid compartment(s) used for the reference measurement(s). This may occur, for example, when the non-invasive measurement is taken from the forearm and the invasive reference measurement is taken from the leg, in areas that have similar capillary density.

One method to aid in obtaining matched references is to use multiple samplings, where two or more reference measurements are taken within a short time. The resulting analyte concentrations may be combined in some manner (for example, averaging) to produce an analyte concentration that is representative of the concentration in the tissue. The multiple measurements may be from the same fluid compartment or from different fluid compartments. This multiple sampling process can serve to reduce the variance due to the measurement method itself, for example, the error inherent in a handheld meter. Furthermore, multiple sampling can help to reduce the effect of site-to-site variations on the reference measurement. Site-to-site variations exist when the analyte concentration is not homogenous in the tissue being sampled. If a reference measurement is taken at one location, it may not be representative of the concentration in another location, even if the locations in question are very close to one another. This is a consequence of analyte diffusion from the capillaries into interstitial fluid, where the analyte concentration close to the capillaries may differ from the analyte concentration further away from the capillaries, especially in times of glucose flux. Multiple sampling, therefore, is a technique that can help to achieve kinetic and spatial matches. In a similar vein, a matched analyte reference may be achieved by sampling a sufficient area, that is, an area that is large enough to appropriately represent the area optically sampled. For example, if the non-invasive sampler samples an area of skin of 5 $mm^2$, then multiple samples could be taken across a nominally similar area of skin, where a nominally similar area encompasses the optically sampled area plus or minus fifty percent of that area.

In another aspect of the invention, an improvement over the prior art is achieved when the matched analyte reference is obtained using a process that ensures that the difference in analyte concentration between the reference fluid compartment and the non-invasively sampled fluid compartment is not clinically significant. One such process involves heating the tissue, which includes any process by which the temperature of the tissue is increased above normal skin temperature, which is typically 34 degrees Celsius. This may include local heating due to electromagnetic radiation, in addition to heating over a larger area by means of other external heat sources. Heating methods can also include rubrifractant application, heating devices, etc. Another process for ensuring that the difference in analyte concentration between the reference fluid compartment and the optically sampled compartment is not clinically significant uses conditions of moderately stable glucose values. Glucose levels are considered to be moderately stable if the blood glucose concentration has changed less than 30 mg/dl in one half hour, or if the rate of glucose change in the blood is less than one mg/dl/minute. Conditions that can result in this state include fasting, absence of recent insulin dosing, and no food or drink intake within the previous two hours.

There will be occasions where the preferred reference measurement may not be available or practical, in which case alternate glucose measurements may be used. However, the particular measurements will depend on the circumstances of the non-invasive measurement. For example, the glucose in forearm blood has been found to be similar kinetically to the glucose in interstitial fluid, so that forearm blood glucose provides an acceptable reference as an alternative to interstitial fluid glucose. Likewise, glucose kinetics in the leg are similar to glucose kinetics in the arm, allowing blood from the leg to be used as a reference.

In one method of the present invention, a matched analyte reference is used when performing subject-specific modifications in the non-invasive spectroscopic measurement of analytes. In this context, a subject-specific modification is any process whereby a reference value (or multiple values) is (are) measured and entered into the processing unit following initial calibration, where the references are associated with spectral measurements and used to modify either a calibration model or future non-invasive spectral measurements and predictions. Tailoring, as described herein, is one type of subject-specific modification. Tailoring is detailed in U.S. Pat. No. 6,157,041 to Thomas et al., which is hereby incorporated by reference.

Figure 2:
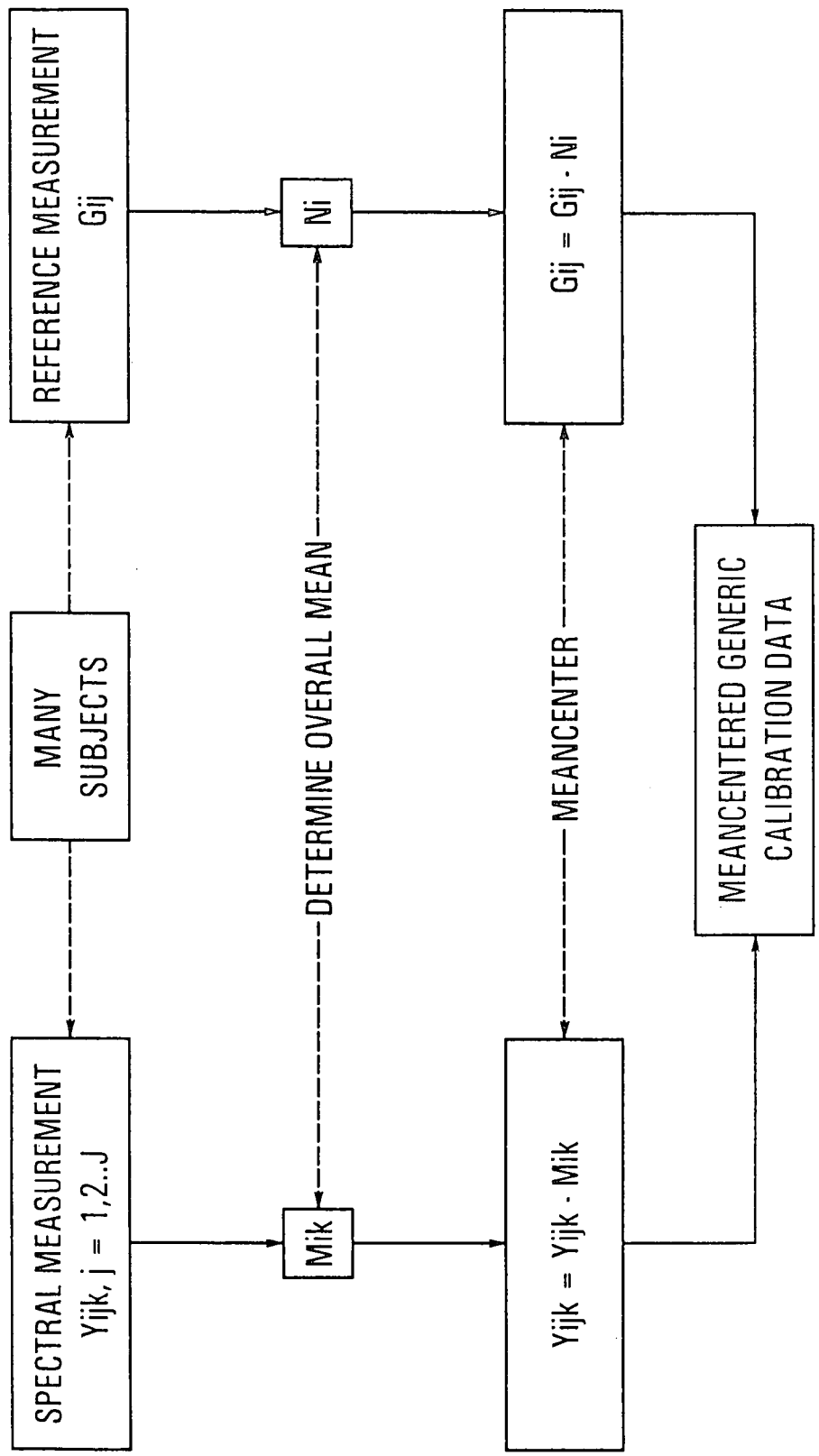
FIG. 2 is a flowchart describing a meancentering process during tailoring.

Each tailored prediction method described herein preferably utilizes "generic" calibration data. Spectroscopic data that have been acquired and processed in a manner that reduces inter-subject spectroscopic variation while maintaining intra-subject variation are herein referred to as generic calibration data. Generic calibration data can be created by a variety of data acquisition and processing methods. In a first processing method, as depicted in the chart of FIG. 2, the generic calibration data are obtained by acquiring a series of spectral measurements from one or more subjects and a matched reference measurement for each subject corresponding to each spectral measurement. The matched reference method can be any of those previously described, such that the agreement between the reference analyte concentration and the analyte concentration in the non-invasively sampled fluid compartment is clinically relevant. An appropriate experimental protocol is needed to provide adequate representation of intra-subject effects that are expected in the future, including those associated with the analyte of interest. The mean spectral measurement and the mean reference measurement for each subject based on the number of measurements from that subject are then formed. The spectral measurements are meancentered by subtracting the mean spectrum of each subject from each of that subject's spectra. The reference measurements are meancentered by subtracting the mean reference measurement of each subject from each of that subject's reference measurements. That is, the subject-specific mean spectral measurements and subject-specific mean reference measurements act as subject-specific subtrahends. The sets of meancentered measurements, both spectral and reference, comprise the generic calibration data.

There are a number of other related ways for creating generic calibration data with a subject-specific subtrahend. For example, the subject-specific subtrahends for the spectral and reference measurements could be some linear combination of each subject's spectral and reference measurements, respectively. In each case, however, the reference analyte information preferably comes from a matched reference analyte method.

In another preferred method for creating generic calibration data, the subject-specific subtrahends for the spectral and reference measurements consist of the mean of the first S spectral measurements of each subject and the mean of the first S reference measurements of each subject, respectively. Alternatively, a moving window reference technique could be utilized wherein the subtrahends are the subject-specific means of the S nearest (in time) spectral and reference measurements, where S is less than the total number of reference measurements made on a particular subject. The value of S can be chosen to fit the constraints of the particular application, neglecting effects due to random noise and reference error.

Once the generic calibration data have been created, such data is then utilized to create a tailored prediction process specific for a particular subject for use in future predictions of the biological attribute. The tailored prediction process can be accomplished in several ways.

The most straightforward and direct way to tailor the prediction process to a given subject is as follows and will be denoted as direct tailoring. First, the generic calibration data are used to develop an intra-subject calibration model for the analyte of interest. This model herein is referred to as a generic model. By design, the generic model will produce predictions that are essentially unaffected by intra-subject spectral variation that is represented in the generic calibration data and not associated with the analyte of interest. On the other hand, the generic model will produce predictions that are appropriately sensitive to the analyte of interest. The generic model is applied directly to at least one spectral measurement from a target subject for whom there are corresponding matched reference measurements. The resulting predictions of the generic model are averaged. The difference between the average of the reference measurements and average prediction is computed. This subject-specific difference is added to the subsequent predictions of the generic model as applied directly to the future spectral measurements from the target subject. The resultant sums comprise the net predictions of the reference measurement corresponding to the future spectral measurements from the target subject. It is important to note that a single generic model can be used in the tailoring process for a number of target subjects. It is clear that, when a matched analyte reference is used in this process, the difference between the average of the reference measurements and the average prediction will be more accurate. Correspondingly, the subject-specific difference that is added to the subsequent predictions of the generic model will be more accurate, and the final non-invasive glucose prediction will also be more accurate.

Figure 3:
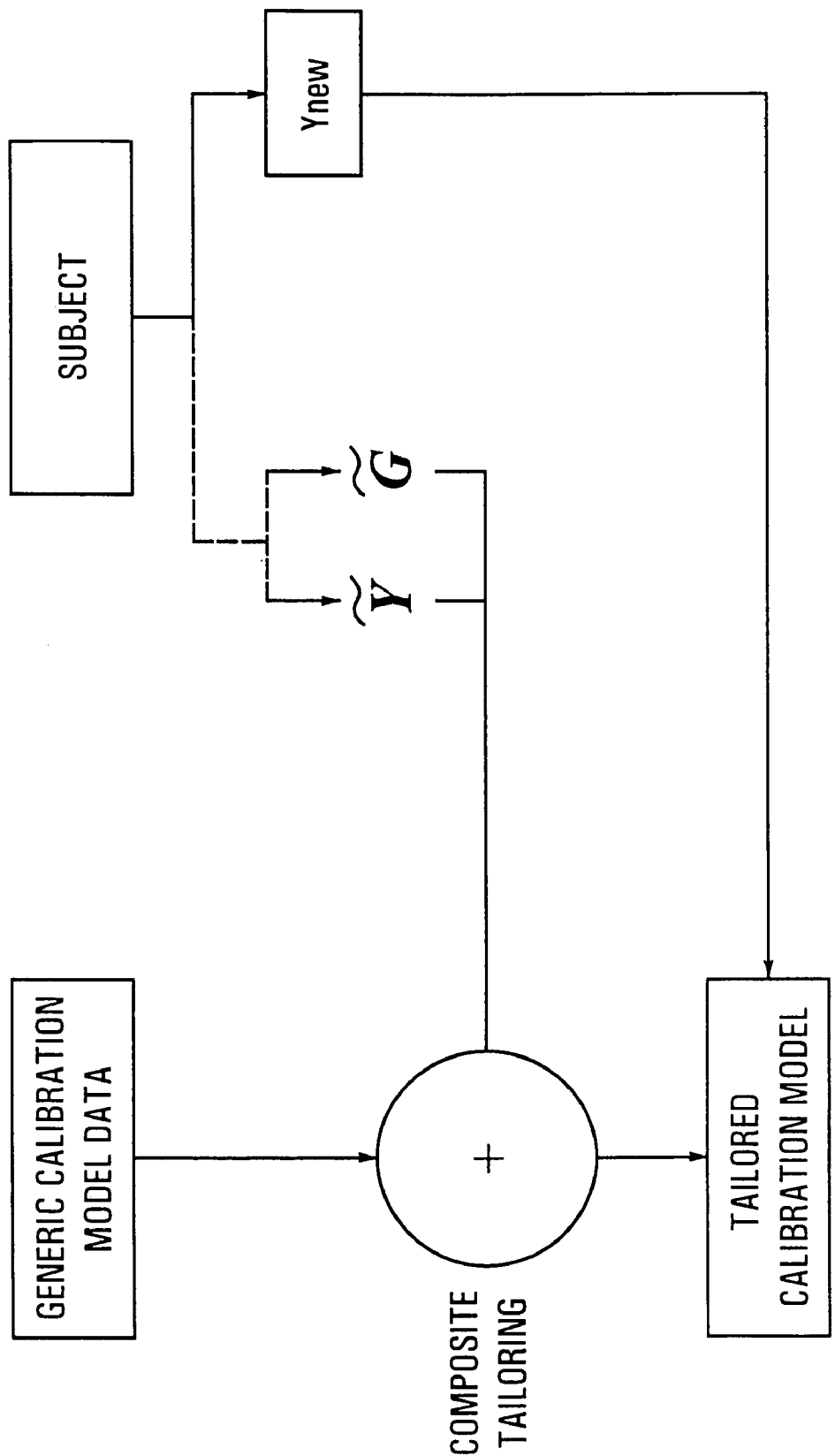
FIG. 3 is a flowchart describing a composite tailoring model (robustification)

A second tailoring embodiment uses a combination of at least two subject reference spectra, matched reference analyte values and the generic calibration data to create a prediction model that is specific for use on the particular subject. The technique by which the calibration data and reference spectra are combined uses a linear combination of the data in absorbance units. The combinations of calibration data and reference data can be done in a structured or random way. Applicants have found that random associations work effectively and are easily implemented. The process of creating these composite data is referred to as robustification. The process is depicted in the flowchart of FIG. 3. The resulting calibration spectra contain the spectra from the particular patient combined with spectral data that contains sources of spectroscopic variation associated with physiological variations, variations associated with sampling techniques, instrument variation and spectroscopic effects associated with the analyte of interest. The composite calibration data can be processed to develop a calibration model. The resulting model will be referred to hereafter as a composite calibration model. The resulting composite calibration model is specific for a particular patient and can be used to generate analyte prediction results for the particular subject.

In the use of either tailored prediction process, reference spectra and matched reference analyte values are utilized, according to the present invention. The reference information is used in combination with the generic calibration data to create a tailored prediction process for use on the particular subject. In general terms, the subject reference information is used to tailor a general processing method for use on a particular subject.

Another type of subject-specific modification can involve a situation where the calibration model is to be specifically chosen for the subject to be predicted. In that case, one or more non-invasive measurements might be collected along with corresponding matched analyte reference values for that subject, and those measurements could be used to empirically choose the most appropriate model for that subject (i.e., the model that measures glucose most accurately for those sample measurements). Other types of subject-specific modifications that involve using non-invasive and matched reference measurements from a subject to modify the model or prediction are also encompassed by the present invention.

While one aspect of the present invention uses matched reference values for subject-specific modifications, a further aspect of this invention is a method for building a calibration model for the non-invasive spectroscopic measurement of analytes, where a matched analyte reference method is used in obtaining the reference measurements associated with the spectral measurements. In doing so, the calibration model displays a more stable relationship between the spectral and analyte measurements, resulting in improved non-invasive analyte predictions. A model with a more stable relationship will have an improved model slope and an improved correlation ($r^2$) between the analyte reference measurements and the non-invasive analyte predictions. Yet another part of this invention is a method for validating a non-invasive calibration model and/or instrument, through the use of matched reference values.

In a preferred embodiment of the present invention, an interstitial fluid glucose reference is used as the matched reference sample in calibrating a non-invasive instrument. Calibration may be performed using a single subject or multiple subjects, in any location, though the most likely locations might include a laboratory, a home or a doctor's clinic setting. The non-invasive measurements, for example, near infrared measurements in the wavelength range 1000 to 2500 nm, using a device such as disclosed in U.S. patent application Ser. No. 09/832,585, filed on Apr. 11, 2001, entitled "System for Non-Invasive Measurement of Glucose in Humans", incorporated herein by reference, are collected from each subject over a period of time during which the subject's glucose varies. The glucose variation may occur naturally or it may be manipulated to achieve a larger range. The range should be at least as large as the range that is expected when measuring glucose in the future. (Note that, in some multiple subject calibrations, multiple measurements from each subject are not necessary, and the glucose range for the model can be achieved by collecting individual measurements from different subjects at different glucose levels.) Along with each of the non-invasive spectral measurements, a reference measurement is collected.

In this embodiment, for a NIR glucose calibration method, interstitial fluid glucose is measured as the matched reference sample. Using a tiny needle, for example, 29-gauge, approximately 0.5 ul of dermal interstitial fluid is extracted from some location on the skin such as the arm or leg and quantitated using, for example, a hand held meter for alternate site testing. Alternatively, in a laboratory setting, a glucose assay could also be used. It is conceivable that in the future, other assays and/or extraction methods for dermal interstitial fluid glucose might be developed, and it is understood that those methods would also be appropriate for use in this invention. Because glucose in the body may change at rates of up to 3–4 mg/dl/min, reference glucose measurements are preferably taken to bracket the non-invasive measurement(s). An estimate of the actual glucose reference at the time of the non-invasive measurement can be calculated, through, for example, interpolation.

In preferred embodiments, other sources of variation may also be incorporated into the calibration data, such as instrumental, environmental and physiological variation that may be expected in the future when using the non-invasive instrument to measure glucose in different conditions. The model can be developed in such a way as to incorporate the various sources of variation into the non-invasive spectra.

When all of the spectral measurements and corresponding glucose reference measurements have been collected, the absorbance spectra (log(intensity)) are generated. They may be processed, for example, to improve noise characteristics in the data. A multivariate calibration method is used to develop a relationship between the spectral measurements and the glucose reference measurements. Examples of such methods include partial least squares (PLS), principal component regression (PCR), classical least squares (CLS), multiple linear regression (MLR) and artificial neural networks (ANN). Errors in the reference measurements reduce the multivariate methods' ability to develop accurate and stable relationships between the spectral and reference measurements, which is why the matched analyte reference method is so important. Those skilled in the art know how to develop and use multivariate methods on these data so that glucose measurements may be made on unknown data in the future.

Another embodiment of the present invention involves using a matched reference method when collecting data following the development of an initial calibration model. For example, data may be required to update the model with knowledge of a new physiological condition or even a new instrumental condition that was not seen in the model. In an alternative embodiment, the new data may be used to modify future spectral measurements in order to make them more similar to spectra in the existing model. In such cases, the subject may be required to collect new non-invasive spectral measurements and corresponding glucose measurements, to be used as matched reference samples, either in their own home or in a doctor's office.

A specific embodiment of this sort involves collecting new NIR spectra and corresponding reference values for a "tailoring" procedure, as described in detail in U.S. Pat. No. 6,157,041 to Thomas et al., which is herein incorporated by reference. The primary purpose of the tailoring procedure is to correct either the model or the new spectra for changes in the subject's physiology over time. Errors in the reference method mean that the correction will not be accurate, and this may even induce larger non-invasive analyte prediction errors in the future. The purpose of the present invention, therefore, is to reduce non-invasive analyte prediction errors of this type.

In utilizing this embodiment, the first step is to generate generic calibration data. This step may be accomplished by utilizing a device such as disclosed in the above detailed U.S. patent application Ser. No. 09/832,585 to measure from one to many subjects, each at a variety of physiological (e.g., taking glucose measurement over a period of time) and spatial (e.g., taking glucose measurements from a variety of locations on the body) states. A preferred method of generating generic calibration data is referred to as meancentering and, as previously stated, is depicted in the flow chart of FIG. 2. Here, let $Y_{ijk}$ be the spectral measurement (e.g., log(intensity)) of the $k^{th}$ wavelength within the $j^{th}$ spectrum from the $i^{th}$ subject. Subject-specific effects are removed as follows. First, form the mean spectrum for each subject. The mean spectrum at the $k^{th}$ wavelength for the $i^{th}$ subject is:

$$M_{ik} = \frac{1}{J_i}\sum_{J=1}^{J_i} Y_{ijk} \quad (1)$$

where $J_i$ is the number of spectra from the $i^{th}$ subject. The appropriate mean spectrum is then removed from each observed spectrum: $Y_{ijk}=Y_{ijk}-M_{ik}$. This process may be referred to as meancentering the spectra by subject.

Associated with each spectrum, we also have a matched reference glucose concentration, preferably from dermal interstitial glucose, but alternatively from forearm or leg blood glucose, $G_{ij}$. The glucose concentrations are also meancentered by subject, resulting in $g_{ij}=G_{ij}-N_i$, where $N_i$ is the mean glucose concentration for the $i^{th}$ subject and defined as:

$$N_i = \frac{1}{J_i}\sum_{J=1}^{J_i} G_{ij} \quad (2)$$

The particular example of meancentered processing is cited to illustrate a specific processing embodiment. At this point, the meancentered spectra and meancentered glucose concentrations are used in the multivariate calibration model development.

Once the generic calibration data has been created, such data are then utilized in forming a tailored prediction process for a particular subject for use in future glucose predictions. This can be accomplished in several ways such as use of a direct-tailoring technique or, alternatively, a composite technique. Common to both methods is a calibration model. A representation of a prediction, $\hat{G}$ using a linear multivariate calibration model (a specific type of calibration model) is $\hat{G}=b_0+b_1 \cdot y_{ij1}^{new}+b_2 \cdot y_{ij2}^{new}+ \ldots +b_k \cdot y_{ijk}^{new}$, where the $b_k$'s are model parameters at each wavelength, k, and the $y_{ijk}^{new}$'s where spectral measurements at each wavelength of a sample, j, from a subject, i. Development of the $b_k$'s from the meancentered spectral data $y_{ijk}$ or other generic calibration data and the reference data $g_{ij}$ is a routine matter for one skilled in chemometrics, as taught by H. Martens et al., *Multivariate Calibration*, (1989), John Wiley, Chichester.

Once the generic model is in hand, it must be tailored (or adapted) for a specific subject. One tailoring method is as follows:

1. Make one (or several) spectral measurement of the target subject's tissue (perhaps varying the spatial position when multiple measurements are obtained at about the same time). Denote the resultant spectrum (or average spectrum when multiple spectra are obtained) by $Y^{ref}$, where $Y^{ref}=\{y^{r1}, y^{r2}, \ldots, y^{rq}\}$. The idea is to obtain very precise spectral measurements for the tailoring process.

2. As close as possible in time with respect to the collection of the spectrum (spectra), an accurate matched reference measurement of in vivo glucose, $G^{ref}$, is obtained from the subject. According to this invention, this reference should be chosen so as to best represent the compartment interrogated by the spectral measurement. The best reference for NIR spectra would be interstitial fluid glucose, but since that may not be readily obtained in a home setting, there are possible alternatives. Forearm blood generally contains a mixture of interstitial fluid, finger capillary blood and venous blood, and is closer kinetically to interstitial fluid glucose than is finger capillary blood glucose during times of glucose flux. This is a preferred tailoring embodiment. Less desirable, but still acceptable, is finger capillary blood glucose during times of stable blood glucose. Finger capillary blood glucose may therefore be used as a reference during the tailoring process when the glucose is not changing rapidly, since the glucose concentration in all body compartments has virtually equilibrated at that time. This is the case prior to insulin dosage and/or food intake.

3. A tailor spectrum is formed (some linear combination of all of the spectra collected in step 1), as is a tailor glucose concentration (again, some linear combination of all glucose concentrations in step 2). Once steps 1–3 have been completed, non-invasive measurements of glucose can be determined in the future as follows.

4. Obtain a new spectral measurement of the subject's tissue, $Y^{new} = \{y^{n1}, y^{n2}, \ldots, y^{nq}\}$.

5. Predict glucose in the new spectrum, using the tailor spectrum and concentration as follows:

$$G^{new} = \sum_{k=1}^{K} \left( (Y_k^{new} - Y_k^{ref}) * \hat{b}_k \right) + G^{ref} \quad (3)$$

Where k is the wavelength index.

A second tailoring technique is the composite technique that is depicted in the flow chart of FIG. 3. With the composite technique, two or more reference measurements, which include both the spectra and the analyte reference values, are made on the particular subject and these data are added in a random fashion to the generic calibration data. The procedure for collecting the reference values so that they are matched to the non-invasive measurement is as described in step 2 of the first tailoring description above. This second tailoring process is represented by the equations:

$$y'_{ijk} = y_{ijk} + y_{ilk}^{ref}, \quad g'_{ij} = g_{ij} + g_{il}^{ref}, \quad (4)$$

where $y_{ilk}^{ref}$ is the $k^{th}$ element of the $l^{th}$ reference spectrum for subject $i$, $g_{il}^{ref}$ is the $l^{th}$ glucose reference value for subject $i$, and a random value of $l$ is chosen for each $i$, $j$ pair The resulting composite data is then used in conjunction with a multivariate analysis technique to generate a calibration model which is subject tailored due to the addition of reference spectral measurements and reference analyte measurements prior to generating the model. The resulting subject-tailored model is then applied to other spectra from the same subject on whom the reference measurements were made. Predictions are made with the resulting calibration model by following standard chemometric practices known to one skilled in the art.

Another embodiment of the present invention enables improved validation of the instrument and calibration model. Validation is the process by which the accuracy and precision of the non-invasive glucose measurements made by the instrument and corresponding calibration model(s) is verified. Validation may be necessary following initial calibration before the non-invasive instrument is used by a patient, and it may also be necessary at different times after the patient has started to use the instrument to verify that the non-invasive glucose measurements are clinically significant. Validation is also necessary in conducting clinical trials to evaluate and/or verify the accuracy and precision of the non-invasive instrument(s). Such validations generally include one or more instruments and one or more subjects for more than one measurement.

In validation, one or more non-invasive measurements are collected along with corresponding glucose reference measurements, as described previously. Non-invasive glucose readings are made using the non-invasive measurements in conjunction with the multivariate model (or multiple models, as the case may be), and the readings obtained are compared statistically to the reference readings using, for example, a root mean square error of prediction (RMSEP) calculation:

$$RMSEP = \sqrt{\frac{\sum_{i=1}^{n} (\hat{G}_i - G_i^{ref})^2}{n-1}} \quad (5)$$

where $\hat{G}_i$ is the glucose predicted by the non-invasive method, $G_i^{ref}$ is the measured glucose reference concentration for that spectral measurement and n is the number of predictions included in the calculation. A small value of RMSEP indicates that the reference values are close to the predicted values.

If a finger capillary glucose reference is compared to a NIR non-invasive glucose reading in times of glucose flux, the readings will be more dissimilar than if a matched glucose reference method is used for the NIR readings. In such a case, the instrument and model performance will be deemed less accurate than the case may truly be. For NIR measurements, the preferred reference is dermal interstitial fluid glucose, but this may not be a straightforward measurement, particularly in the home setting. Alternative procedures are possible. A preferred embodiment for a home setting is to use blood glucose from the forearm or leg, for example, measured with an alternate site home glucose meter. The glucose concentration in this blood, as described previously, is more similar to the glucose concentration in the interstitial fluid that the NIR light interrogates than is the glucose concentration in finger capillary blood during times of glucose flux in the body. An alternative is to collect invasive finger capillary glucose measurements at a time during which it is known that the glucose in the body is not changing rapidly; this will generally be the case immediately prior to an insulin dose and corresponding meal intake.

A comparison of glucose reference measurements and NIR non-invasive glucose measurements was conducted. NIR reflectance spectra between 4200 and 7200 cm$^{-1}$ were collected on an FTIR instrument from one subject over approximately three hours. The subject presented himself at the clinic in a hyperglycemic state and was given intravenous insulin over this time to reduce his glucose level. Glucose was also given intravenously to prevent his glucose levels from dropping too low (below 75 mg/dl).

The NIR measurements were bracketed by reference glucose readings from three sources: dermal interstitial fluid, forearm blood and finger capillary blood. These reference measurements were taken every 10 minutes. Capillary fingertip blood glucose (CBG) was assayed using an enzymatic-based analyzer (YSI 2700 SELECT, Yellow Springs, Ohio). In addition to glucose, hematocrit was determined for these samples. Approximately one microliter of interstitial fluid (ISF) was extracted from forearm skin using a needle-based technique. A small, 29-gauge needle, 11 millimeters long, was mounted in a flat plate. The bevel of the needle protrudes 1.5 millimeters through the side of the plate presented the dermis. A spring mounted on the dermal-presented face of the plate provides local pressure to "squeeze" the ISF out of the dermis. The fluid flows through the lumen of the needle and into a piece of microbore polyethylene tubing. After collection, the ISF glucose concentration is assayed using a small-volume commercial test strip and meter. The strips and meters are calibrated using a dilute-plasma surrogate of ISF against the enzymatic-based analyzer. It is recognized that other ISF assay methods could be utilized. The forearm blood samples were obtained via a lancet on the forearm, and their glucose concentration was measured using a Therasense meter in its standard operation mode. Like capillary fingertip blood, ISF glucose (ISFG) and forearm blood glucose assays were made pre- and post-NIR sampling. All types of glucose readings were interpolated in time to produce readings valid at the time of the non-invasive measurements.

Figure 14:
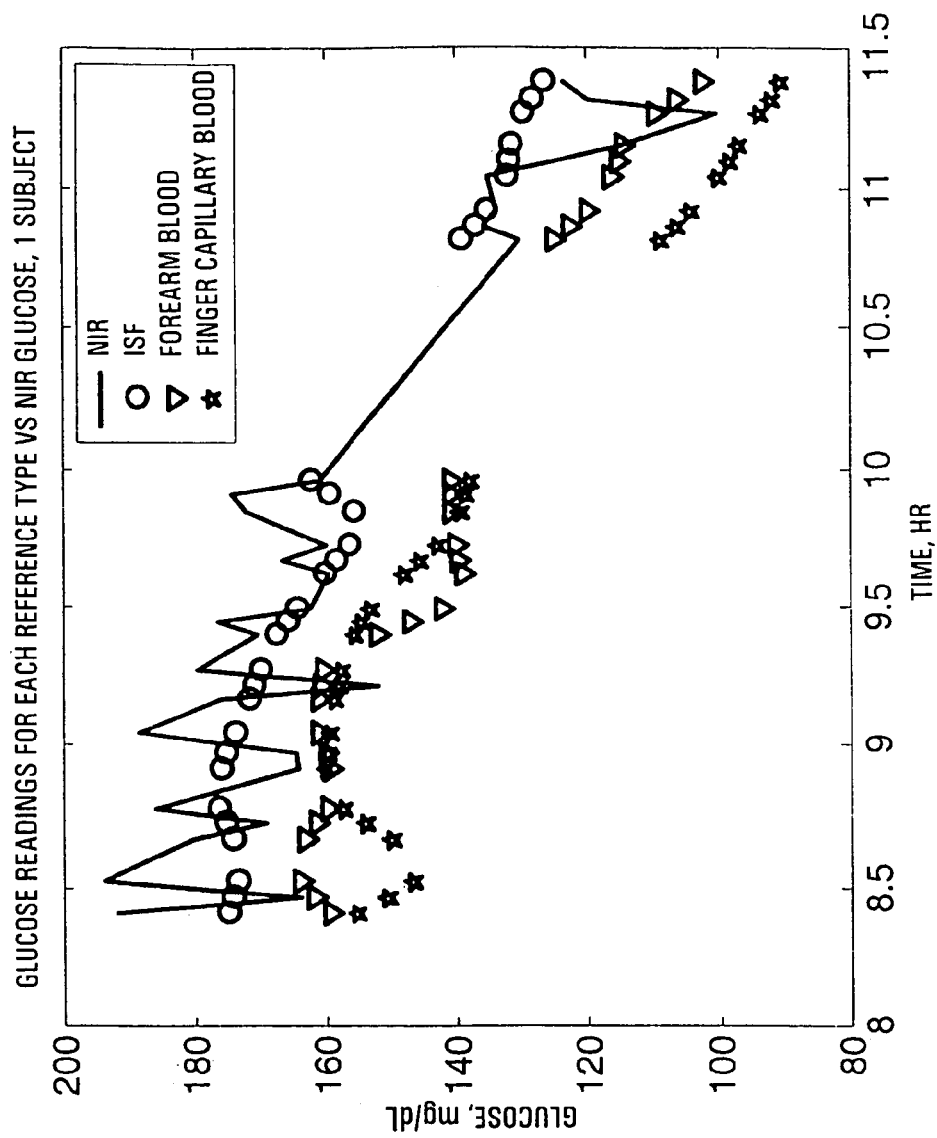
FIG. 14 is a graph depicting NIR glucose predictions over time along with each reference measurement.

FIG. 14 displays the NIR glucose predictions over the three-hour period, along with the corresponding reference measurements for that time. The plot shows that there is a time lag between the finger capillary glucose readings and the NIR glucose readings, which is believed due to the fact that the NIR beam interrogates mainly interstitial fluid. The interstitial fluid glucose readings are, therefore, much closer to the NIR readings than are the other glucose reference values. The finger capillary glucose measurements decrease much more quickly than the other two reference measurements, since the finger capillaries are among the first fluid compartments to respond to glucose and insulin changes in the body. The interstitial fluid compartment, on the other hand, is the slowest compartment to respond, since this compartment relies on diffusion kinetics. Forearm (lancet) blood glucose is between the two, since it can contain combinations of capillary blood, venous blood and interstitial fluid. This shows how the reference measurement can either be very similar or matched to, or very different from, the non-invasive measurements. The following show how this can affect the calibration, tailoring and validation of in vivo glucose measurements.

A calibration study was also conducted. NIR reflectance spectra between 4200 and 7200 cm−1 were collected on an FTIR instrument from 56 subjects over the course of 8 weeks. At each visit, the NIR measurements were bracketed by reference glucose readings from two sources, dermal interstitial fluid and finger capillary blood. These reference measurements were obtained in the manner described previously. Like capillary fingertip blood, ISF glucose (ISFG) assays were made pre- and post-NIR sampling.

Figure 4A:
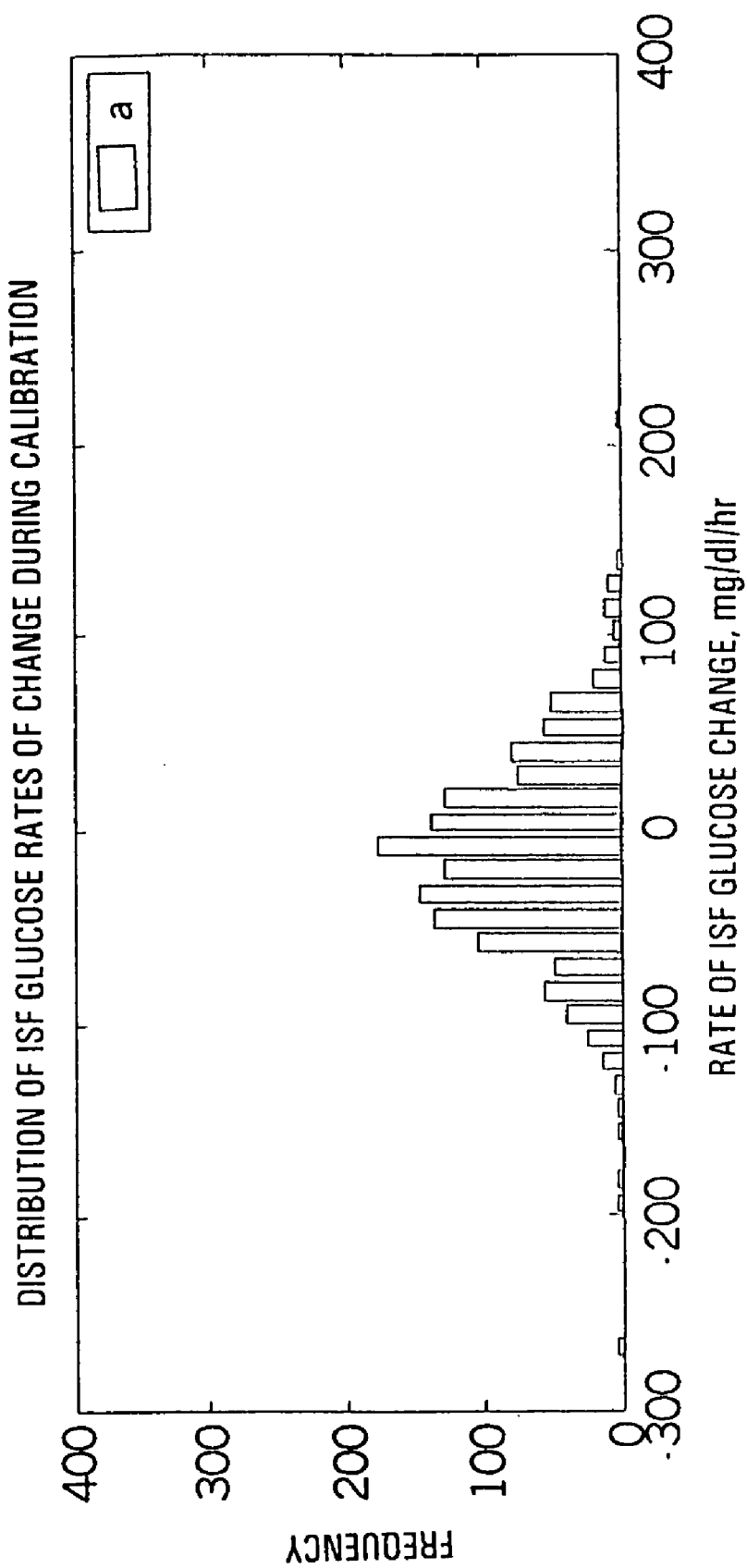
FIG. 4 depicts the distribution of glucose rates of change seen during a representative calibration.

Both types of glucose readings were interpolated in time to produce readings valid at the time of the non-invasive measurements. The subjects visited the clinic once or twice a day and were not required to fast or eat at any particular time. In other words, the rate of glucose flux was variable in this study. FIGS. 4A and 4B show histograms detailing the rates of change of glucose seen during the course of this study. FIG. 4A depicts interstitial fluid glucose, and FIG. 4B depicts finger capillary blood glucose. Clearly, there are many cases of extreme glucose change where the glucose in the finger capillaries is unlikely to match the glucose in the dermal interstitial fluid. This is also demonstrated in FIG. 5, which shows corresponding glucose reference values for (a) dermal interstitial fluid and (b) capillary blood for a single subject over the course of data collection.

Figure 6:
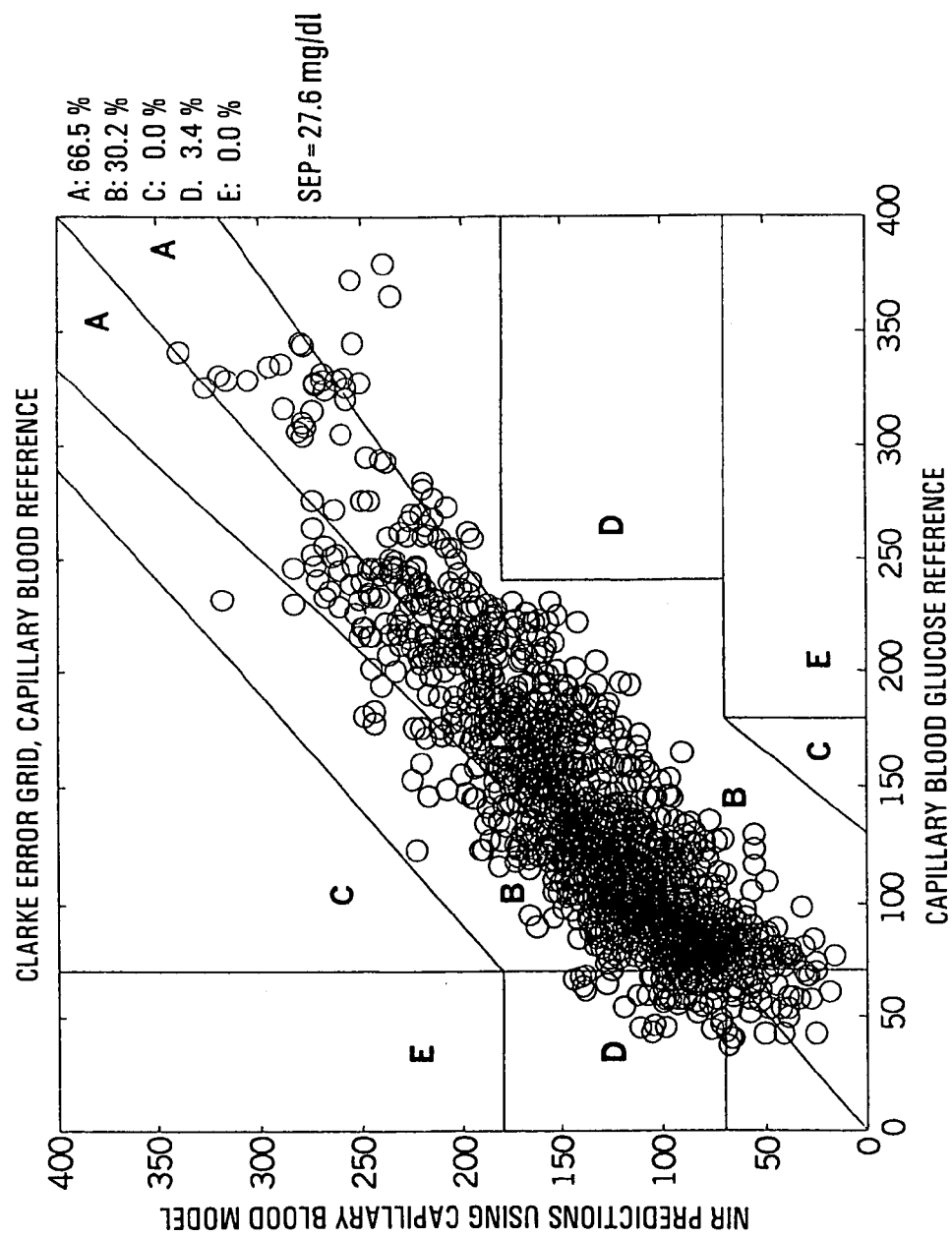
FIG. 6 depicts the Clarke error grid obtained when finger capillary blood glucose was used as a reference during calibration.
Figure 7:
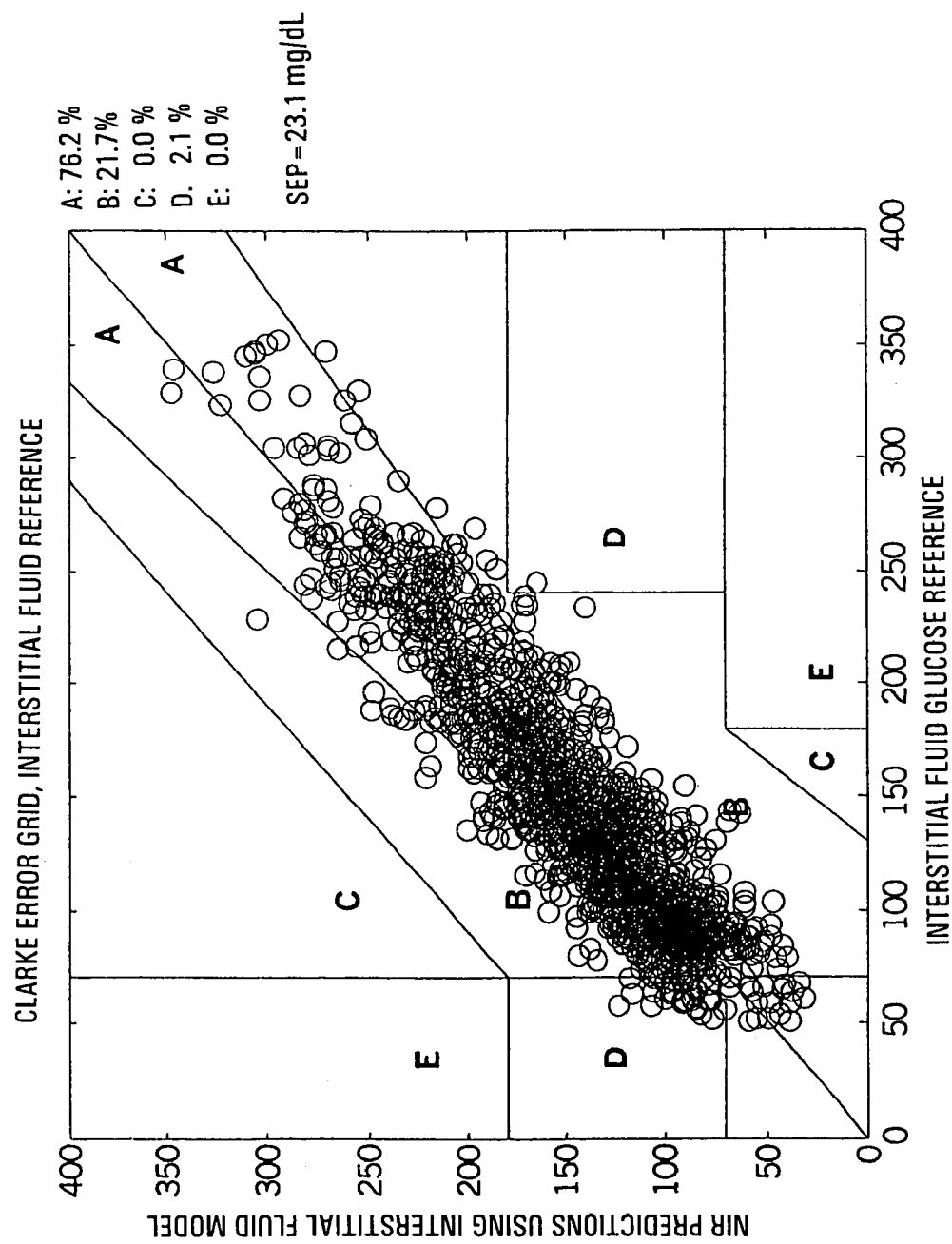
FIG. 7 depicts the Clarke error grid obtained when interstitial fluid glucose was used as a reference during calibration.
Figure 8A:
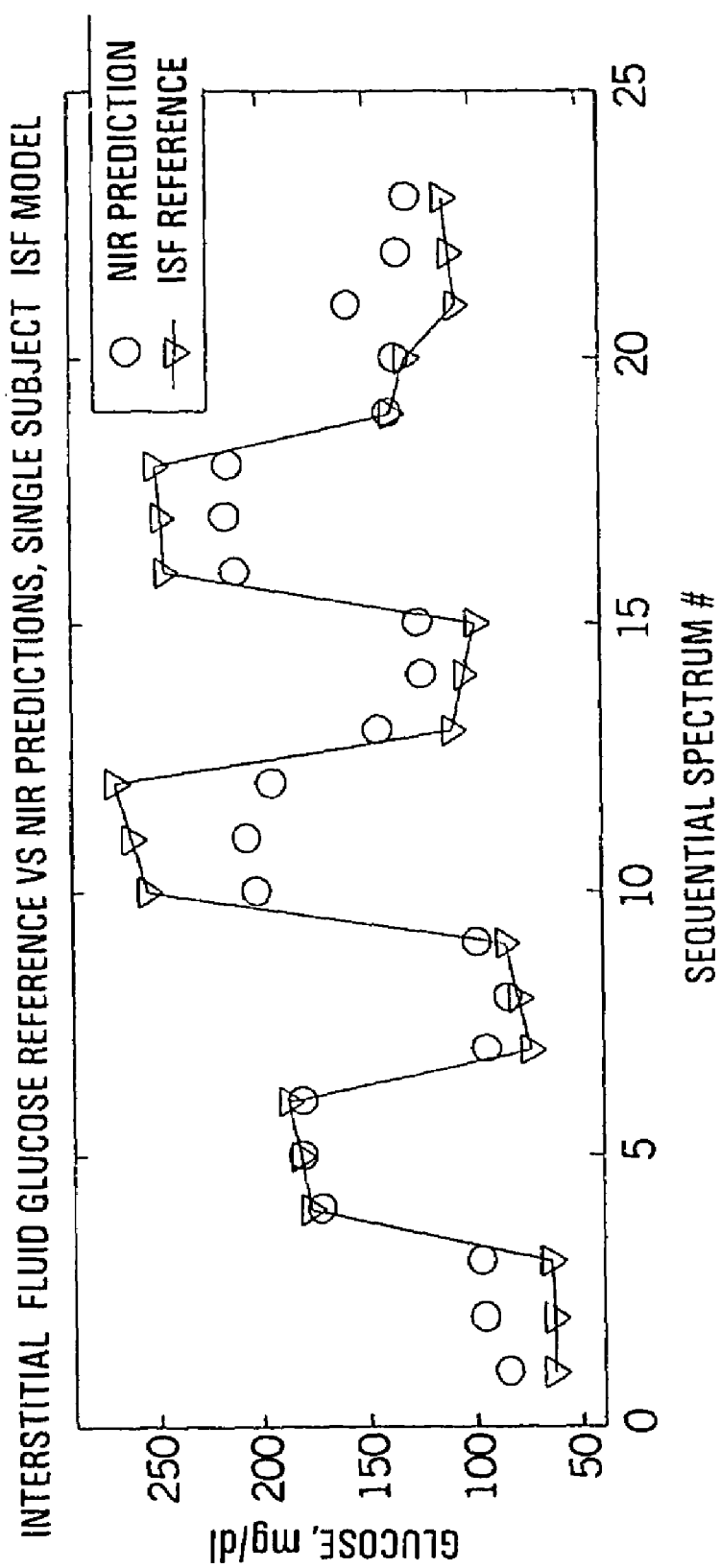
FIG. 8A depicts NIR predictions compared with interstitial fluid glucose reference.
Figure 8B:
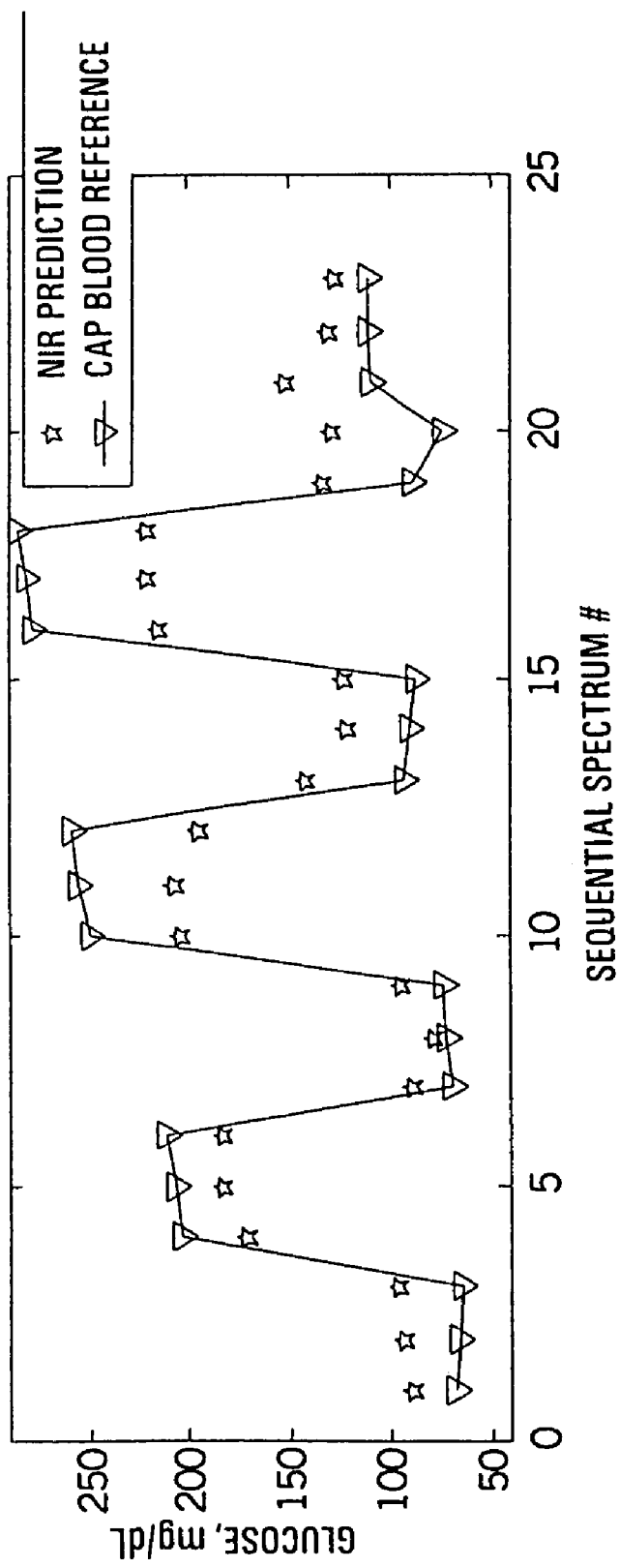
FIG. 8B depicts NIR predictions compared with capillary blood glucose reference.

Following data collection, the spectral data were converted to absorbance spectra. PLS was used to develop models relating the NIR absorbance spectra to dermal interstitial fluid glucose and also relating the NIR absorbance spectra to finger capillary blood glucose. Concentration outliers were removed from the models. Spectral outliers were also removed according to standard procedures. Spectral F ratio outliers and Mahalanobis distances outliers were removed in this case, but other spectral outlier techniques are also available and known to those practiced in the art. A cross-validation procedure (by subject) was carried out for both cases. Cross-validation is a procedure known to those knowledgeable in the art of multivariate analysis. FIG. 6 shows a Clarke Error Grid for the capillary blood reference, and FIG. 7 shows a similar plot for the dermal interstitial fluid reference. In the case of the interstitial fluid glucose, regions A and B contain a larger percentage of the data than is true for the capillary blood reference. Furthermore, the standard error of prediction is lower for the interstitial fluid glucose model, and the slope and $r^2$ are also improved over the finger capillary glucose model. This implies that the relationship between the reference glucose measurements and the non-invasive spectral measurements in the model is better for the interstitial fluid than for the capillary blood. FIGS. 8A and 8B show non-invasive glucose measurements, interstitial fluid glucose reference measurements and finger capillary blood glucose measurements for a single subject. FIG. 8A plots assayed interstitial fluid glucose reference sample results versus NIR non-invasive predictions using an ISF developed model. FIG. 8B plots assayed capillary blood glucose reference sample results versus NIR predictions using a capillary blood developed model. Clearly, the NIR glucose readings follow the interstitial fluid glucose readings more closely than they follow the finger capillary blood readings. Building the model with a matched reference has allowed improved glucose readings following calibration.

Experimental studies on tailoring were also completed. The NIR and interstitial fluid glucose data from the previous studies were used in measuring glucose in a follow-on study where nine subjects were measured over the course of a month. In every case, the model did not contain the subject who was to be measured.

Figure 9:
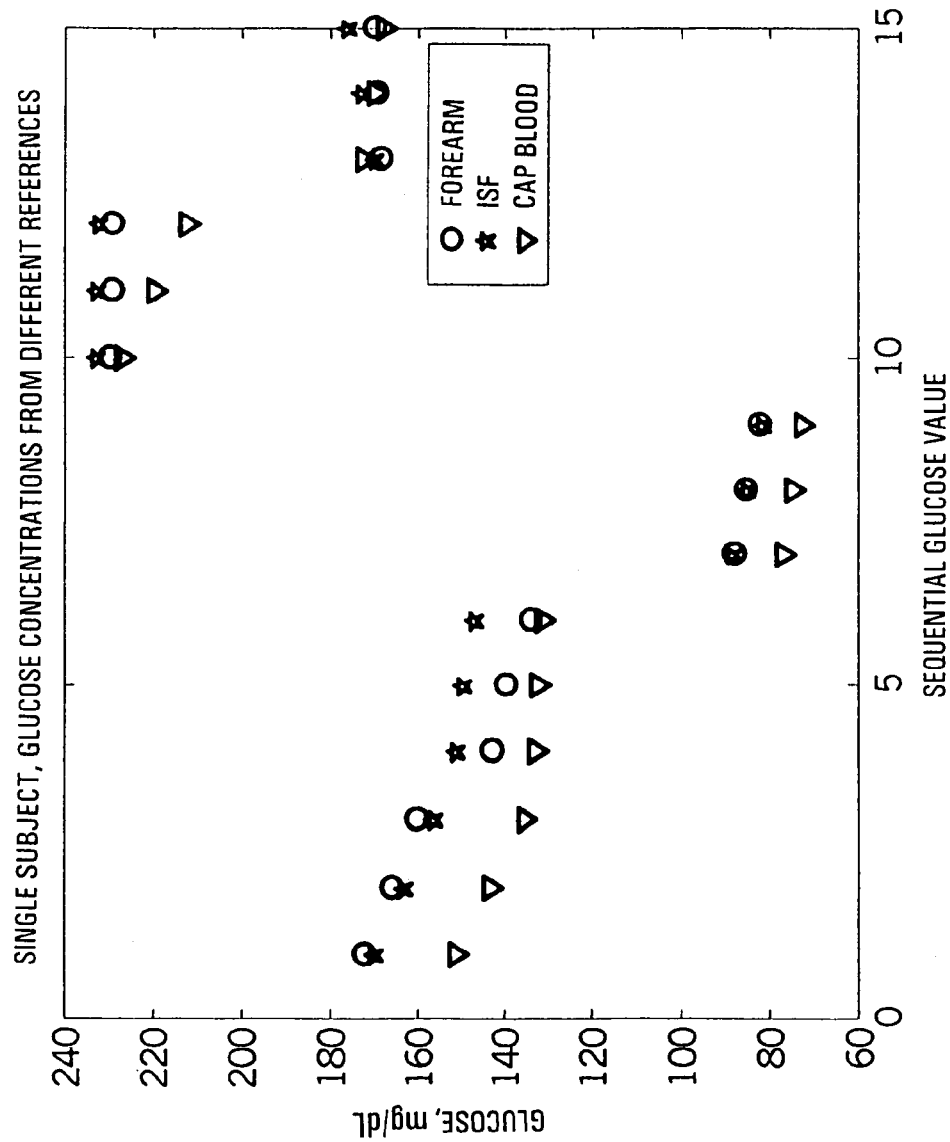
FIG. 9 depicts glucose concentrations seen for a single subject from interstitial fluid measurements, forearm blood measurements and finger capillary blood measurements.

Each subject visited the clinic four times before the non-invasive glucose measurement period commenced. This was to be the "tailoring" period. Their glucose levels were not controlled in any way during this time. At each visit, a number of NIR spectral measurements were collected, and those measurements were bracketed in each case by three types of glucose reference measurements, including finger capillary glucose (measured using the YSI), dermal interstitial fluid glucose (measured using a Therasense meter calibrated for plasma glucose) and forearm blood glucose (measured using a Therasense meter in its standard operation mode). The values were interpolated to obtain glucose readings valid for the time of the NIR measurements. FIG. 9 shows the three types of references for one subject. For each subject, the mean spectral measurement and mean reference glucose measurement (one for each type of reference) were calculated (following outlier detection and removal) and used as the "tailor data".

Figure 10:
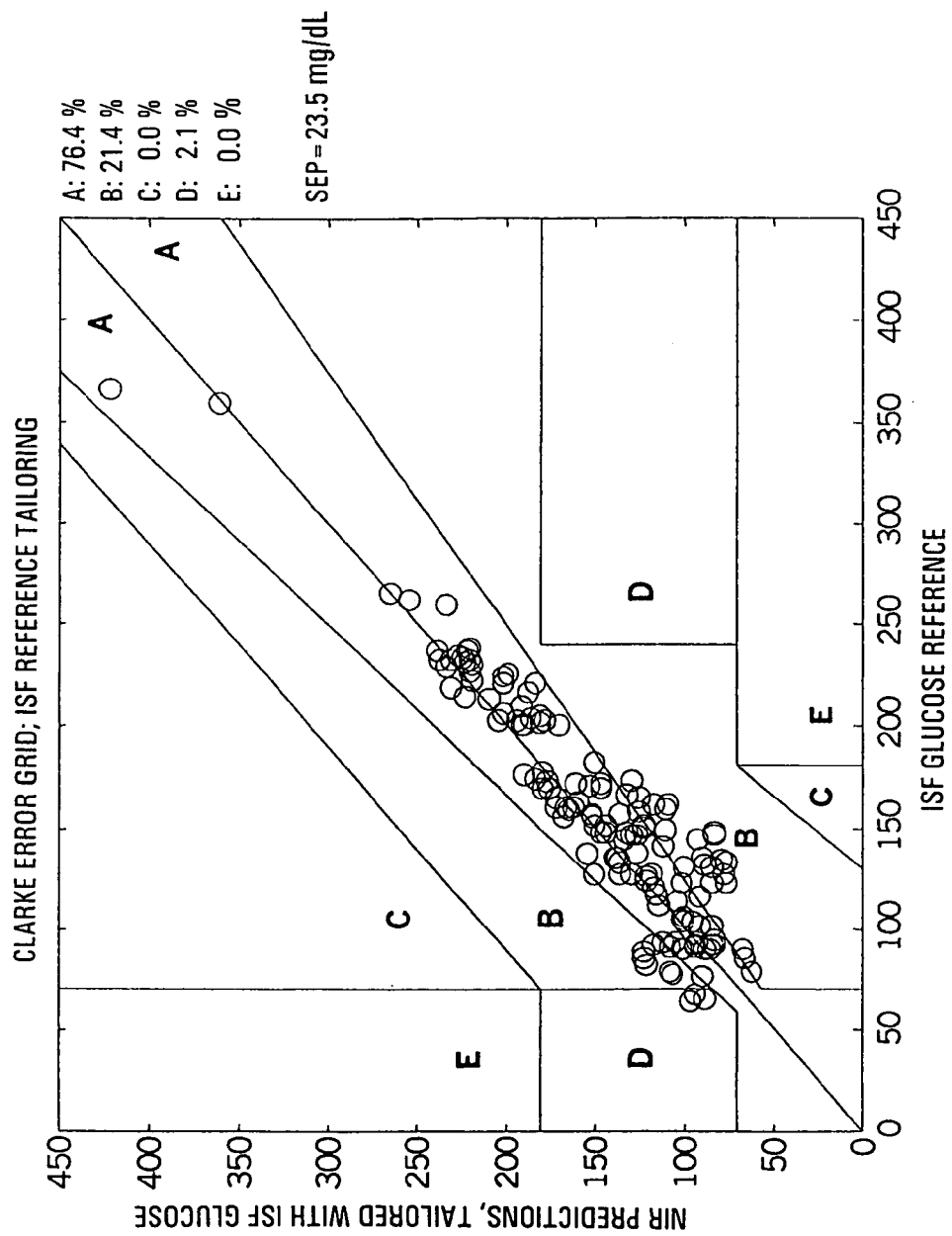
FIG. 10 depicts a Clarke Error grid for NIR predictions (obtained with interstitial fluid glucose tailor references) versus interstitial fluid glucose reference.
Figure 11:
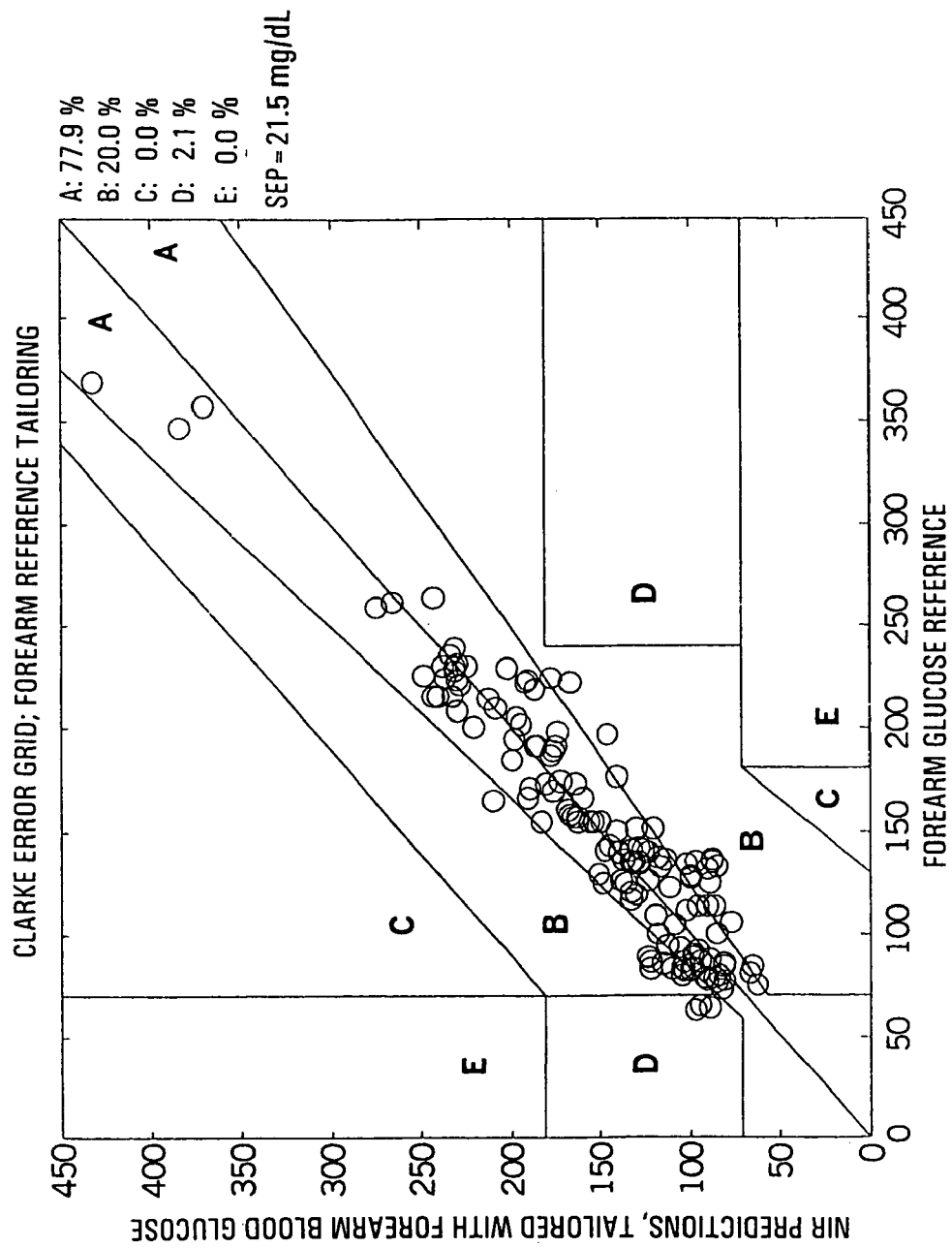
FIG. 11 depicts a Clarke Error grid for NIR predictions (obtained with forearm blood glucose tailor references) versus forearm blood glucose reference.
Figure 12:
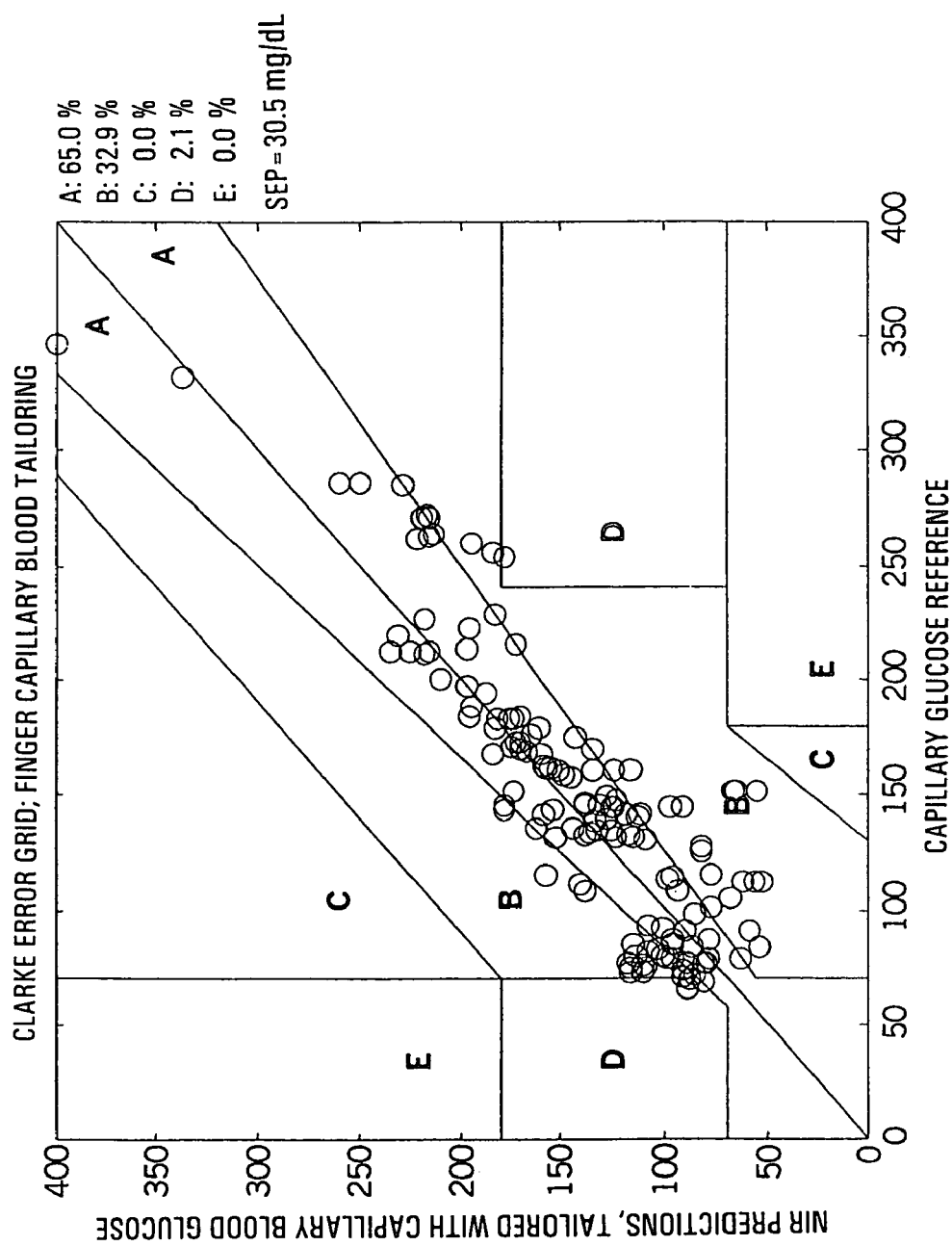
FIG. 12 depicts a Clarke Error grid for NIR predictions (obtained with capillary blood glucose tailor references) versus capillary blood glucose reference.

Following the tailor period, the subjects visited the clinic eight more times. Again, their glucose values were not manipulated, and in each case, the data collection proceeded as it did during the tailoring period. Each predicted non-invasive glucose reading (G) was made according to equation (3). Again, the model data were obtained as described previously. Non-invasive readings were obtained for the three cases where the tailor concentration was derived from dermal interstitial fluid glucose, forearm blood glucose and finger capillary glucose. FIGS. 10 through 12 show the non-invasive readings obtained in each case, compared to the reference values obtained in each case. In this case, the correlation between the forearm blood reference and the non-invasive readings are best, but the interstitial fluid glucose readings are extremely similar due to the kinetic similarities between glucose in interstitial fluid and glucose in forearm blood. (Forearm blood, when collected using a lancet, may even contain some portion of interstitial fluid). While an interstitial fluid glucose reference is expected to be the best reference for the NIR measurements, in this case that is not apparent because of (a) errors in the assay technique and (b) site to site variations in glucose concentration in the interstitial fluid. It is, therefore, clear that the choice of best reference method should take measurement technique errors into consideration. The finger capillary readings are worst, as expected, since there is often a difference between the glucose concentration in the finger capillaries and the tissue interrogated by the NIR. In a home setting, the forearm blood glucose is a preferred embodiment, due to the current difficulties in obtaining interstitial fluid glucose readings.

These and various other advantages and features of novelty that characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

What is claimed is:

1. A method for performing modifications to calibration models in the non-invasive spectroscopic measurement of an analyte or attribute of tissue, the method comprising the steps of:
    providing a means for irradiating tissue with infrared energy;
    providing an output element, the output element operatively connected to a means for measuring a spectrum;
    irradiating tissue with the infrared energy so that there is absorption of at least a portion of the infrared energy in the tissue;
    collecting at least a portion of the infrared energy exiting the tissue through the output element and measuring the resulting spectrum;
    collecting at least one matched reference sample that is assayed to determine at least one reference value of the analyte or attribute of tissue; and
    using the at least one reference value with the spectral measurement to perform a modification to the calibration model;
    wherein the matched reference sample is a fluid taken from a tissue compartment that is kinetically matched to the tissue which is irradiated.

2. The method of claim 1, wherein the matched reference sample is interstitial fluid.

3. The method of claim 1, wherein the matched reference sample is bulk fluid in the tissue.

4. The method of claim 1, wherein the matched reference sample is fluid obtained from a limb.

5. The method of claim 1, wherein the matched reference sample is lancet blood obtained from a forearm.

6. The method of claim 1, wherein the matched reference sample is a fluid taken from a tissue compartment that is spatially matched to the tissue which is irradiated.

7. The method of claim 1, wherein site-to-site variations are reduced through multiple collection of matched reference samples of the tissue over a sufficient area.

8. The method of claim 7, where the area optically sampled and the area used for procurement of multiple matched reference samples are nominally similar.

9. A method for performing subject specific modifications in the non-invasive spectroscopic measurement of an analyte or attribute of tissue, the method comprising the steps of:
    providing a means for irradiating tissue with infrared energy;
    providing an output element, the output element operatively connected to a means for measuring a spectrum;
    irradiating tissue with the infrared energy so that there is absorption of at least a portion of the infrared energy in the tissue;
    collecting at least a portion of the infrared energy exiting the tissue through the output element and measuring the resulting spectrum;
    collecting reference samples that are kinetically matched to the irradiated tissue and assaying the reference samples for the analyte or attribute of tissue; and
    using the assayed reference samples with the spectral measurements to perform a subject-specific modification.

10. A method for building a calibration model for the non-invasive spectroscopic measurement of an analyte or attribute of tissue, the method comprising the steps of:
    providing a means for irradiating tissue with infrared energy;
    providing an output element, the output element operatively connected to a means for measuring optical information;
    irradiating tissue with the infrared energy so that there is absorption of at least a portion of the infrared energy in the tissue;
    collecting at least a portion of the infrared energy exiting the tissue through the output element and measuring a resulting spectrum;
    collecting matched reference samples and assaying the matched reference samples for the analyte or attribute of tissue; and
    using the reference sample measurements along with the infrared measurements to build a multivariate calibration model;
    wherein the matched reference sample is a fluid taken from a tissue compartment that is kinetically matched to the tissue which is irradiated.

11. The method of claim 10, wherein the matched reference sample is interstitial fluid.

12. The method of claim 10, wherein the matched reference sample is the bulk fluid in the tissue.

13. The method of claim 10, wherein the matched reference sample is the fluid obtained from a limb.

14. The method of claim 10, wherein the matched reference sample is lancet blood obtained from a forearm.

15. The method of claim 10, wherein the matched reference sample is a fluid from a tissue compartment that is spatially matched to the tissue which is irradiated.

16. The method of claim 10, wherein the area irradiated and the area used for procurement of the matched reference samples of the tissue are nominally similar in size.

17. A noninvasive method for measuring a biological attribute in human tissue of a specific subject comprising the steps of:
    providing an apparatus for measuring infrared absorption, the apparatus including an energy source emitting infrared energy at multiple wavelengths, an input element, an output element and a spectrum analyzer;

coupling the input and output elements to the human tissue;

irradiating the tissue through the input element with multiple wavelengths of infrared energy with resulting absorption of at least some of those wavelengths;

collecting at least a portion of the non-absorbed infrared energy with the output element followed by determining the intensities of the infrared energy; and predicting the biological attribute of the specific subject utilizing a model, wherein the subject specific prediction method uses one or more previously obtained matched reference samples assayed for the biological attribute and one or more previously obtained spectral measurements from the specific subject, and the matched reference sample is taken from a tissue compartment that is kinetically matched to the tissue which is irradiated.

18. The method of claim 17, wherein the matched reference sample is interstitial fluid.

19. The method of claim 17, wherein the matched reference sample is bulk fluid in the tissue.

20. The method of claim 17, wherein the matched reference sample is fluid obtained from a limb.

21. The method of claim 17, wherein the matched reference sample is lancet blood obtained from a forearm.

22. The method of claim 17, wherein the matched reference sample is a fluid from a tissue compartment tat is spatially matched to the tissue which is irradiated.

23. The method of claim 17, wherein the area irradiated and the area used for procurement of the matched reference sample are nominally similar.

24. A method for validating noninvasive measurement performance in the non-invasive spectroscopic measurement of an analyte or attribute of tissue, the method comprising the steps of:

providing a means for irradiating tissue with infrared energy;

providing an output element, the output element operatively connected to a means for measuring optical information;

irradiating tissue with the infrared energy so that there is absorption of at least a portion of the infrared energy in the tissue;

collecting at least a portion of the infrared energy exiting the tissue through the output element and measuring a resulting spectrum;

collecting at least one matched reference sample and assaying the sample for the analyte or attribute of tissue; and using the matched reference sample measurement, the spectral measurements and a pre-existing multivariate calibration model to evaluate the non-invasive measurement performance;

wherein the matched reference sample is a fluid taken from a tissue compartment that is kinetically matched to the tissue which is irradiated.

25. The method of claim 24, wherein the pie-existing model contains data from multiple subjects.

26. The method of claim 24, wherein the pre-existing model contains data from a single subject.

27. The method of claim 24, wherein the matched reference sample is interstitial fluid.

28. The method of claim 24, wherein the matched reference sample is bulk fluid in the tissue.

29. The method of claim 24, wherein the matched reference sample is fluid obtained from a limb.

30. The method of claim 24, wherein the matched reference sample is lancet blood obtained from a forearm.

31. The method of claim 24, wherein the matched reference sample is a fluid from a tissue compartment that is spatially matched to the tissue which is irradiated.

32. A method for correcting predictions in the non-invasive spectroscopic measurement of an analyte or attribute of tissue, the method comprising the steps of:

providing a means for irradiating tissue with infrared energy;

providing an output element, the output element operatively connected to a means for measuring a spectrum;

irradiating tissue with the infrared energy so that there is absorption of at least a portion of the infrared energy in the tissue;

collecting at least a portion of the infrared energy exiting the tissue through the output element and measuring a resulting spectrum;

collecting at least one matched reference sample and assaying the sample for the analyte or attribute of tissue; and using the at least one matched reference sample measurement with the spectral measurements to correct future non-invasive analyte predictions;

wherein the matched reference sample is a fluid taken from a tissue compartment that is kinetically matched to the tissue which is irradiated.

* * * * *

UNITED STATES PATENT AND TRADEMARK OFFICE
CERTIFICATE OF CORRECTION

PATENT NO. : 7,027,848 B2 Page 1 of 1
APPLICATION NO. : 10/116269
DATED : April 11, 2006
INVENTOR(S) : Mark Ries Robinson et al.

It is certified that error appears in the above-identified patent and that said Letters Patent is hereby corrected as shown below:

Column 23
Line 27, delete "tat", and insert therefor -- that --.

Column 24
Line 8, delete "pie-existing", and insert therefor -- pre-existing --.

Signed and Sealed this

Twenty-second Day of August, 2006

JON W. DUDAS
*Director of the United States Patent and Trademark Office*